US010212494B1

(12) United States Patent
Struhsaker et al.

(10) Patent No.: US 10,212,494 B1
(45) Date of Patent: Feb. 19, 2019

(54) METHOD AND SYSTEM FOR MONITORING PHYSICAL ASSETS

(71) Applicant: TIONESTA, LLC, San Antonio, TX (US)

(72) Inventors: Paul Struhsaker, San Antonio, TX (US); Paul Posner, San Antonio, TX (US); Michael Landers, San Antonio, TX (US); Nicholas Armstrong, San Antonio, TX (US)

(73) Assignee: TIONESTA, LLC, Austin, TX (US)

( * ) Notice: Subject to any disclaimer, the term of this patent is extended or adjusted under 35 U.S.C. 154(b) by 0 days.

(21) Appl. No.: 15/799,348

(22) Filed: Oct. 31, 2017

(51) Int. Cl.
*H04Q 9/00* (2006.01)
*H04L 29/08* (2006.01)
*H04W 92/20* (2009.01)
*H04W 84/12* (2009.01)

(52) U.S. Cl.
CPC ............ *H04Q 9/00* (2013.01); *H04L 67/125* (2013.01); *H04Q 2209/43* (2013.01); *H04Q 2209/47* (2013.01); *H04W 84/12* (2013.01); *H04W 92/20* (2013.01)

(58) Field of Classification Search
CPC .. H04Q 9/00; H04Q 2209/43; H04Q 2209/04; H04L 67/125; H04W 84/12; H04W 92/20
See application file for complete search history.

(56) References Cited

U.S. PATENT DOCUMENTS

| 2004/0095907 | A1* | 5/2004 | Agee | H04B 7/0417 |
| | | | | 370/334 |
| 2016/0088473 | A1* | 3/2016 | Feher | G06F 21/32 |
| | | | | 455/411 |
| 2017/0302511 | A1* | 10/2017 | Foster | H04L 41/0803 |
| 2018/0014312 | A1* | 1/2018 | Ezaki | H04W 72/042 |

* cited by examiner

*Primary Examiner* — Nader Bolourchi
(74) *Attorney, Agent, or Firm* — Osha Liang LLP

(57) ABSTRACT

A system for monitoring physical assets in a monitored environment. The system includes monitoring devices attached to monitored assets, and configured to collect monitoring data from the monitored assets, a first access point, configured to receive the collected monitoring data from the monitoring devices and to process the collected monitoring data, an Internet of Things (IoT) link established between each of the monitoring devices and the access point, and an IoT communication protocol overlay that enables synchronized uplinks from the monitoring devices to the first access point via the IoT links. The IoT communication protocol overlay governs transmissions of monitoring data by the monitoring devices to the access point. The system further includes a hub/cloud platform configured to receive the processed monitoring data from the first access point, perform data analytics on the processed monitoring data; and provide a user interface that enables a user to monitor the physical assets.

32 Claims, 18 Drawing Sheets

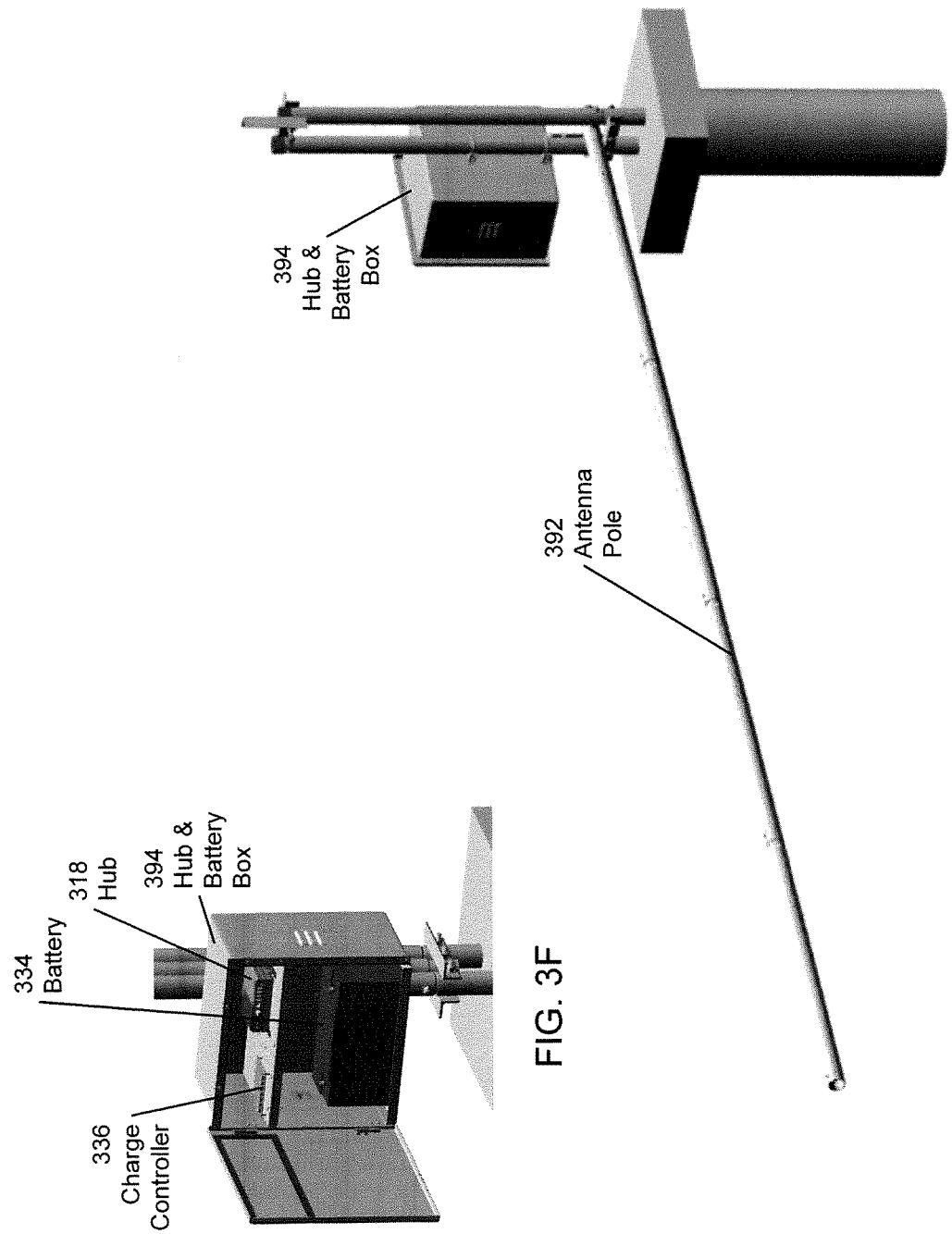

METHOD AND SYSTEM FOR MONITORING PHYSICAL ASSETS

BACKGROUND

Availability of the status of various physical assets can be beneficial or even essential. For example, it may be useful to track the location of moving items or persons, for various reasons such as to provide security, to optimize certain operations, e.g., in industrial environments or logistic applications, and/or to provide useful instructions to a tracked person. Further, monitoring stationary objects may also be useful. Such a stationary object may be, for example, a sensor that can be queried to obtain information about the environment surrounding the sensor.

SUMMARY

In general, in one aspect, the invention relates to a system for monitoring physical assets in a monitored environment. The system comprises: monitoring devices attached to monitored assets, and configured to collect monitoring data from the monitored assets; a first access point, configured to receive the collected monitoring data from the monitoring devices and to process the collected monitoring data; an Internet of Things (IoT) link established between each of the monitoring devices and the access point; an IoT communication protocol overlay that enables synchronized uplinks from the monitoring devices to the first access point via the IoT links, wherein the IoT communication protocol overlay governs transmissions of monitoring data by the monitoring devices to the access point; and a hub/cloud platform configured to: receive the processed monitoring data from the first access point; perform data analytics on the processed monitoring data; and provide a user interface that enables a user to monitor the physical assets.

In general, in one aspect, the invention relates to a system for monitoring physical assets in a monitored environment. The system comprises: a two-tier access point comprising a first tier broadband communication interface and a second tier narrowband communication interface, and configured to: receive, using the narrowband interface, monitoring data from monitoring devices that are attached to monitored assets and configured to collect the monitoring data from the monitored assets; and transmit, using the broadband interface, the received monitoring data to a hub/cloud platform that provides a user interface enabling a user to monitor the physical assets.

BRIEF DESCRIPTION OF DRAWINGS

FIGS. 3A-3G show access points of a system for monitoring assets, in accordance with one or more embodiments of the invention.

DETAILED DESCRIPTION

Figure 1A:
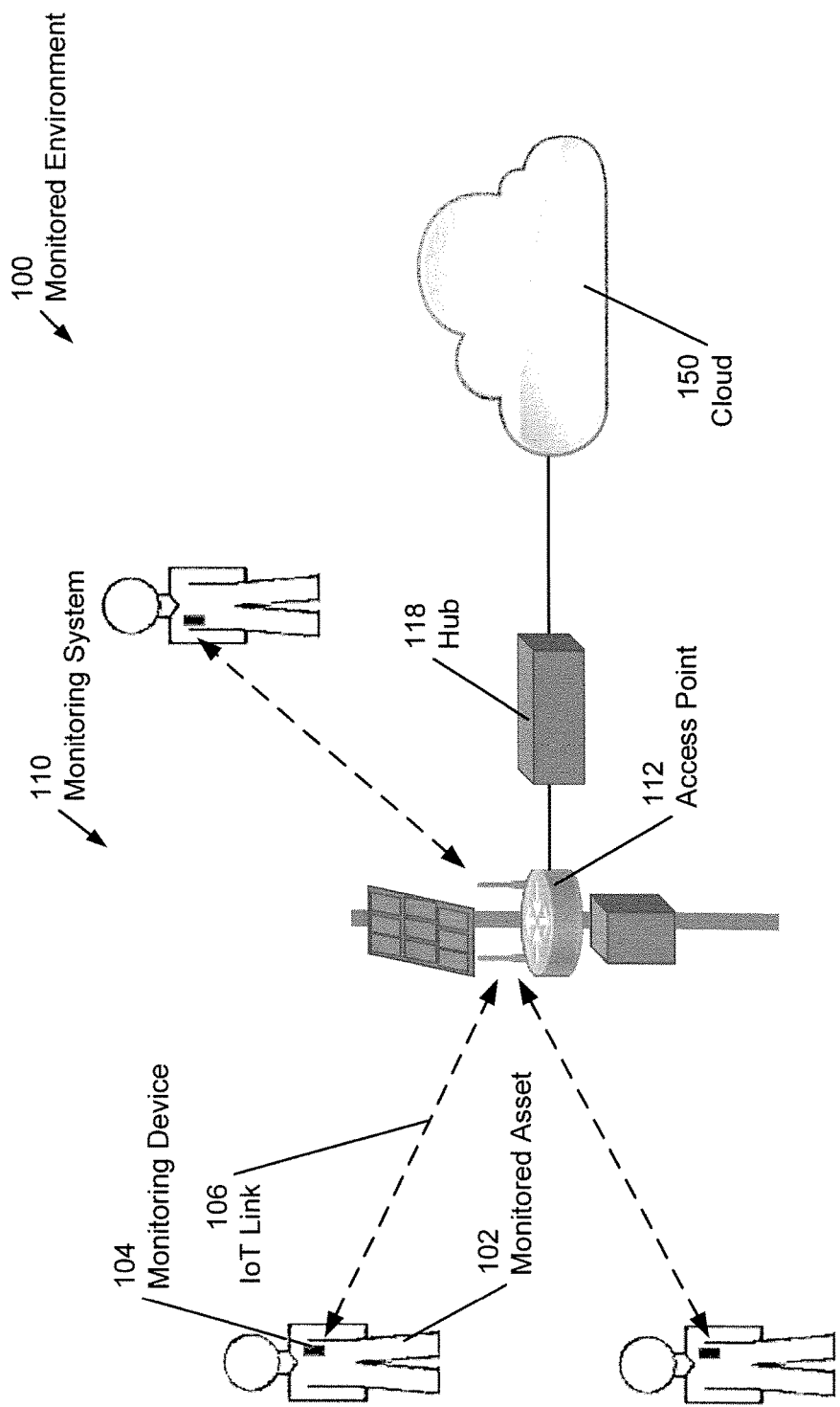
FIGS. 1A-1H show systems for monitoring assets, in accordance with one or more embodiments of the invention.

Specific embodiments of the invention will now be described in detail with reference to the accompanying figures. Like elements in the various figures are denoted by like reference numerals for consistency. Like elements may not be labeled in all figures for the sake of simplicity.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements or limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1A-8, any component described with regard to a figure, in various embodiments of the invention, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments of the invention, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that, one or more of the steps shown in the flowcharts may be omitted, repeated, and/or performed in a different order than the order shown. Accordingly, the scope of the invention should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

In general, embodiments of the invention are directed to methods and systems for monitoring assets. An asset may be anything of interest and/or value for which it is valuable to gather information about the status of the asset. Consider, the following examples:

A hospital that is specialized in the treatment of patients with dementia. If these patients are allowed to move freely within the hospital environment, it may be important to be able to determine their location at any time. Further these patients may suffer from additional conditions that may require continuous monitoring of other variables such as heart rate, blood pressure, etc.

In a luggage transportation system of a major airport, the ability to locate any luggage item at any time, while being processed by the luggage transportation system, would be highly beneficial.

In the oil and gas industry, it may be beneficial to monitor pipelines or other equipment to ensure safety and productivity.

In a warehouse, it may be useful to track employees, goods and/or equipment to optimize operations.

Those skilled in the art will appreciate that the invention is not limited to the above examples. Embodiments of the invention may be used in any environment, including commercial, industrial, residential and natural environments of any size to monitor moving or stationary assets including, but not limited to, humans, animals, devices, products, or any other type of item. Further, the monitoring includes obtaining any type of information such as a location or a measurement of any variable.

FIGS. 1A-1H show systems for monitoring assets, in accordance with one or more embodiments of the invention. Turning to FIG. 1A, a monitored environment (100), in accordance with one or more embodiments of the invention, is shown. The monitored environment (100) may be any type of environment that is monitored using the monitoring system (110). A monitored environment may be, for example, an outdoor environment, e.g., in the oil and gas industry, or an area where environmental monitoring is performed, e.g., in a national park. A monitored environment may also be an indoor environment, for example, a warehouse, a school, a hospital, a prison, etc. A monitored environment may also include a combination of indoor and outdoor environments, e.g., when a campus of a public or private institution is monitored. Any environment that is equipped with a monitoring system (110) may be considered a monitored environment (100).

Within the monitored environment (100), monitored assets (102), may be tracked or monitored by the monitoring system (110). Monitored assets (102) may include stationary and/or moving assets. A moving asset may be a person, an animal, equipment (e.g., a forklift truck), goods, products or other items, including luggage, shipments such as boxes or containers, etc. A stationary asset may be anything equipped with sensors to monitor function and/or environmental conditions. Examples for such stationary assets include weather stations, pumps, pipelines, refrigeration equipment, air quality sensors, etc. The monitoring may be performed by a monitoring device (104) that is carried by the monitored asset or that is attached or installed on the monitored asset.

In one or more embodiments of the invention, a monitored asset (102) may further be controlled via the monitoring system (110). A monitoring device (104) may interface with the monitored asset (102) to, for example, activate or deactivate functions, switch modes, etc. If the monitoring device (104) is also used for sensing, a closed loop operation via the monitoring system (110) may be implemented. Based on sensed conditions, the monitored asset may be controlled in order to change the sensed conditions.

An access point (112), in one or more embodiments of the invention, is configured to communicate with the monitoring devices (104) of the monitored assets (102) via an Internet of Things (IoT) link (106). The access point may further interface with a hub (118), which may perform processing of the data received from the monitored assets via the access points, as further described below. In one or more embodiments of the invention, data gathered from the monitored assets is uploaded to a cloud environment (150), from where they may be accessible to users. Additionally or alternatively, the data may also be locally accessible via the hub or via the access point, as further described below. Each of the components of the system for monitoring assets is subsequently described in detail, with reference to FIGS. 2A-7.

Figure 1B:
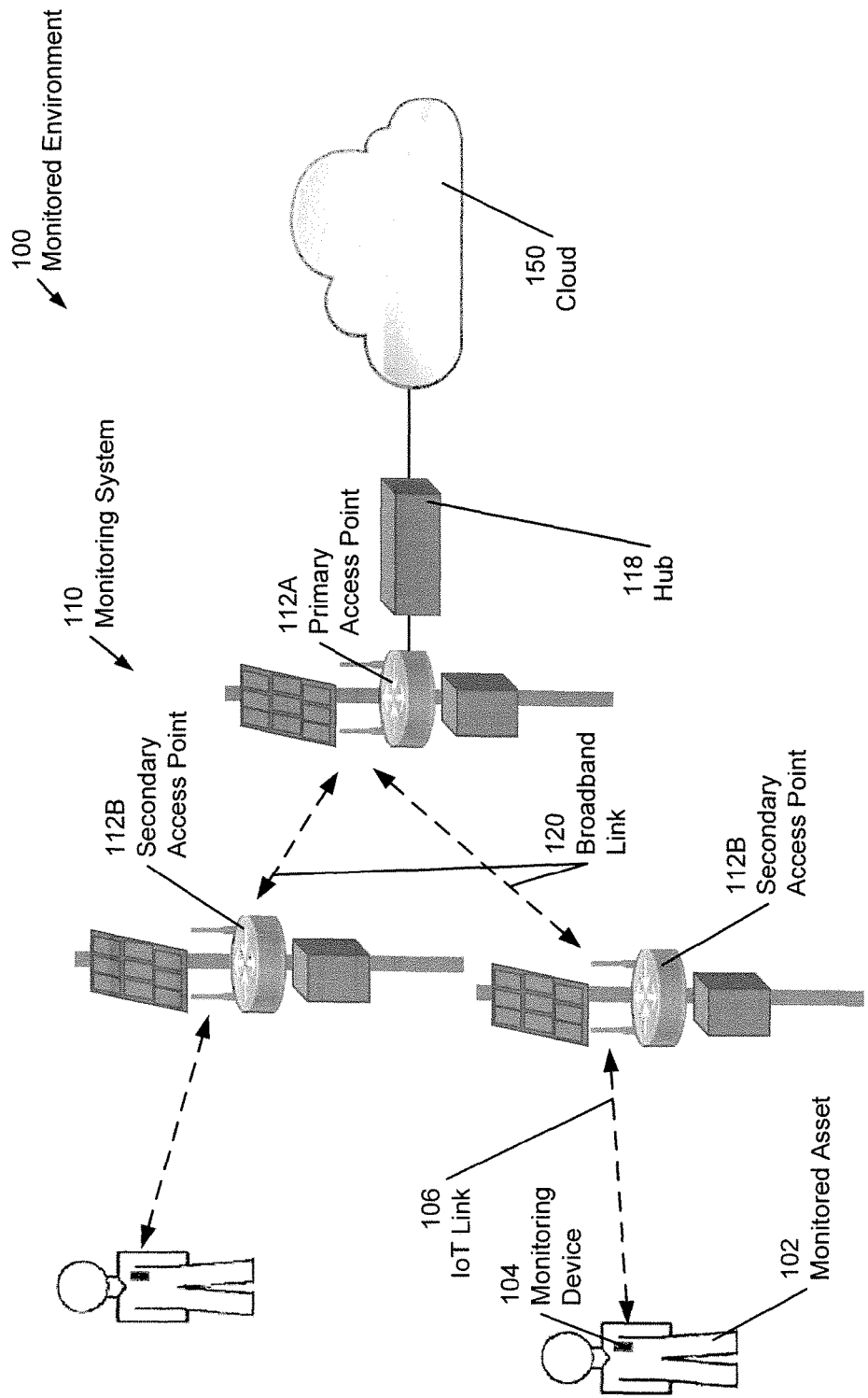

Turning to FIG. 1B, an alternative configuration of a system for monitoring assets (110), in accordance with one or more embodiments of the invention, is shown. Unlike the system shown in FIG. 1A, the system of FIG. 1B includes multiple access points (112A, 112B). Each access point may have a limited range that may depend on the transmission power of the access point, but also on the transmission power of the monitoring devices (104) of the monitored assets (102). Accordingly, in order to cover larger environments (100) with monitoring services, multiple access points may be placed at different locations in the environment. FIG. 1B shows a primary access point (112A) and two secondary access points (112B). While the primary access point (112A) may directly interface with the hub (118), e.g., using a wired broadband link such as an Ethernet interface, the secondary access points may interface with the primary access point (112A) using a broadband link (120) such as a wireless local area network (WLAN) based on, e.g., the Wi-Fi standard. Using additional access points, distributed across the monitored environment (100), larger areas may thus be covered by the system for monitoring assets (110). Those skilled in the art will appreciate that various configurations of multiple access points are feasible without departing from the invention. For example, systems for monitoring assets may include any number of access points to monitor environments of any size. Further, multiple access points may directly interface with the hub (similar to the primary access point (112A)). Alternatively or additionally, multiple access points may increase the monitored area using a daisy chain configuration (i.e., tertiary access points may interface with the secondary access points, analogous to how the secondary access points interface with the primary access point). Further, in hybrid configurations, some access points may be daisy-chained, whereas other access points may directly interface with the hub. In one embodiment of the invention, an access point or multiple access points may be directly connected to the cloud, e.g., when a reliable connection to the cloud is continuously available.

Figure 1C:
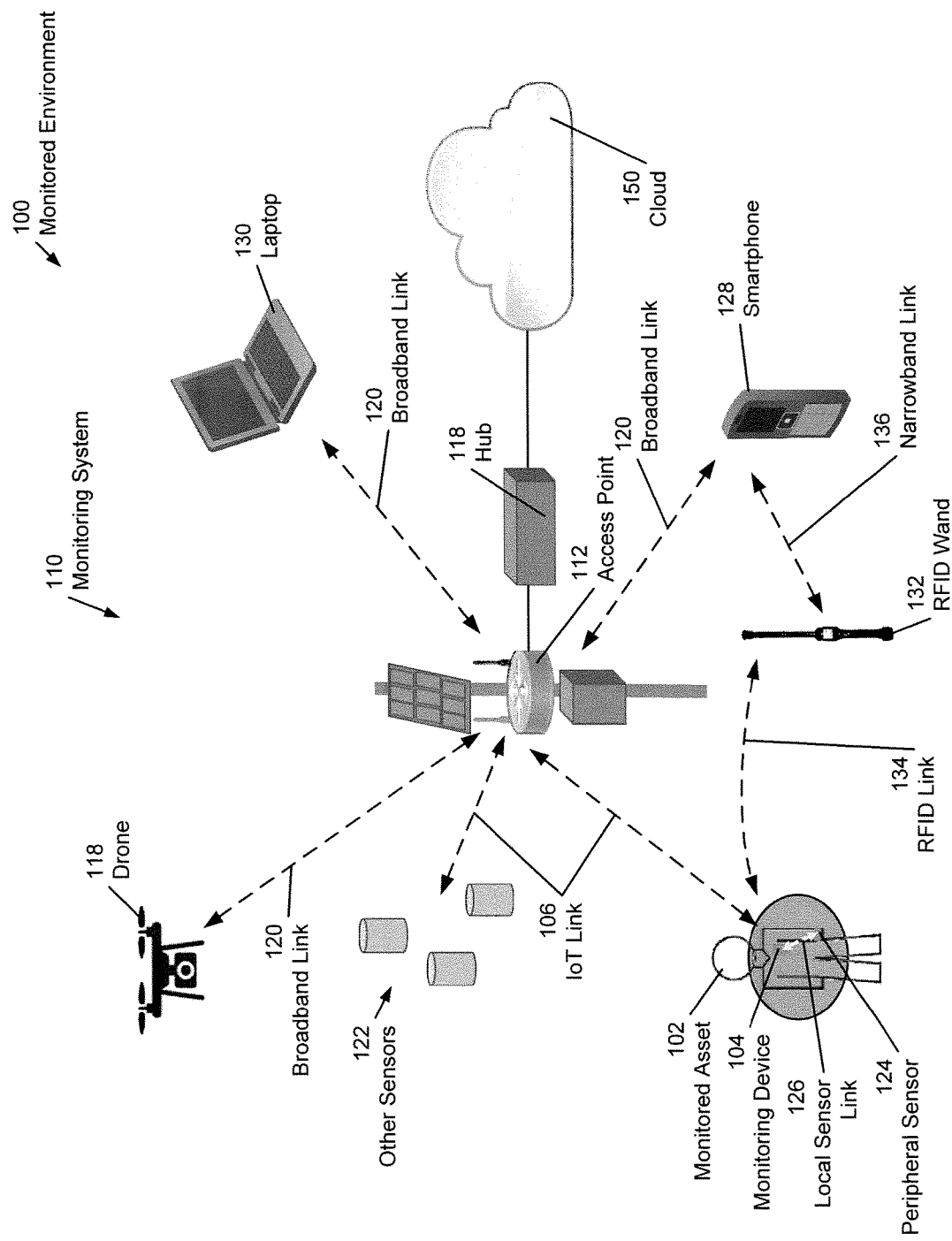

Turning to FIG. 1C, another alternative configuration of a system for monitoring assets, in accordance with one or more embodiments of the invention, is shown. The system includes additional components that may facilitate the use of the monitoring system and/or provide additional features. In one embodiment of the invention, the broadband link (120) of the access point (112) is used to provide user access to the monitoring system (110). More specifically, user devices such as smartphones (128) or laptops (130) may connect to the access point (112) via the broadband link (120) in order to obtain monitoring data, to configure the monitoring system, etc. Data that is provided by the monitoring devices (104) and/or monitoring device data that has been previously collected, processed and/or stored by the hub (118) may be obtained via a hub/cloud platform, described in FIGS. 2A and 2B.

In one or more embodiments of the invention, the broadband link may further be used to interface additional devices with access points (112) of the monitoring system (110). In FIG. 1C, a drone (118) is shown, communicating with the access point (112) via the broadband link (120). The drone may further enhance the monitoring capabilities of the monitoring system (110). The drone may, for example, be equipped with a camera and/or other sensors and may be in contact with various access points, depending on the drone's current location in the monitored environment (100). The drone may further not necessarily be in continuous contact with an access point and may, instead, operate autonomously and may only require periodic contact with an access point. One or more drones (118) may be used to visually inspect environments. Multispectral cameras and/or mosaic photography may be used to monitor environmental conditions and/or activity in the monitored environment using additional analytics software.

Other sensors that rely on a broadband link (160) via one of the access points (112) may be part of the monitoring system as well. For example, cameras that are equipped with a Wi-Fi interface may be used to visually monitor certain areas of the monitored environment (100). Such cameras may include motion detection to detect activities including expected or desired activity, but also unexpected activity, such as intrusions. Additionally or alternatively, cameras may provide still photos, video clips or live videos and/or alarms based on a detection of certain events in the videos or photos. In addition, the broadband link (160) may be used for any other purposes such as voice over IP and/or for any other high data rate service.

In one or more embodiments of the invention, the monitoring system (110), using the IoT link (106), interfaces not only with the monitoring devices (104), but also with other sensors (122). The other sensors may perform environmental measurements such as air temperature, humidity, or may be used to monitor equipment such as pumps, storage tanks, pipelines, etc.

One or more embodiments of the invention further support additional sensing equipment in the form of peripheral sensors (124). A peripheral sensor may be used to acquire additional measurements that may not be obtainable by the monitoring device (104) itself. The peripheral sensors thus further extend the monitoring functionalities provided by the monitoring device (104). Any number of peripheral sensors (124) may be used in conjunction with a monitoring device (104). A local sensor link (126) may transmit the measurements obtained by the peripheral sensor (124) to the monitoring device (104), which may relay these measurements to one of the access points (112). An exemplary peripheral sensor is further discussed below, with reference to FIG. 5.

In one or more embodiments of the invention, the access point (112) is a two-tier access point equipped with a first tier broadband communication interface and a second tier narrowband communication interface. The first tier broadband communication interface provides the broadband link (120) and the second tier narrowband interface provides the IoT link (106). While the narrowband link may provide coverage of a comparatively large area at a reduced data rate that may be particularly suitable for monitoring devices (104) and other sensors (122), the broadband link may provide coverage of a comparatively smaller area at a higher data rate that may be suitable to serve other devices such as laptops (130), smartphones (128), or other broadband equipment, including drones (118), cameras (not shown), etc. The broadband link may further be used to establish a mesh with other access points, as previously shown in FIG. 1B. In one embodiment of the invention, the monitoring system includes a three-tier network that, in addition to the two tiers of the access point, includes a third tier formed by the local sensor link (126), as previously described.

FIG. 1C further shows a radio frequency identification (RFID) wand. The RFID wand may be used, in proximity of an RFID transmitter to read out basic information provided by the RFID transmitter. The RFID transmitter may be a component of the monitoring device (104) or of a peripheral sensor (124) and may provide static information such an ID. Consider, for example, the use of monitoring devices (104) to track luggage at an airport. Airport security may then be able to obtain the identity of luggage equipped with a monitoring device, using the RFID wand. The RFID wand (or stationary RFID readers) may further be used in other security and/or monitoring applications such as check-through scenarios at facility entries and exists, clock-in/clock-out applications, etc. The RFID wand may be equipped with a GPS unit, enabling obtaining a location at the time when RFID information is obtained from an RFID transmitter. Additionally or alternatively, the RFID wand may be equipped with an IoT interface enabling the RFID wand (132) to communicate with one or more access points (112) in order to obtain a location and/or to upload RFID information obtained from an RFID transmitter. Further, RFID wands, in accordance with one or more embodiments of the invention, may be equipped with a narrowband communication interface to establish a narrowband link (136), e.g., a Bluetooth link to another device such as a smartphone (128) or a laptop (130). The narrowband link may enable a user to access RFID data either spontaneously, e.g. as an RFID transmitter is read, or in bulk readouts, after a number of RFID transmitters have been scanned.

Figure 1D:
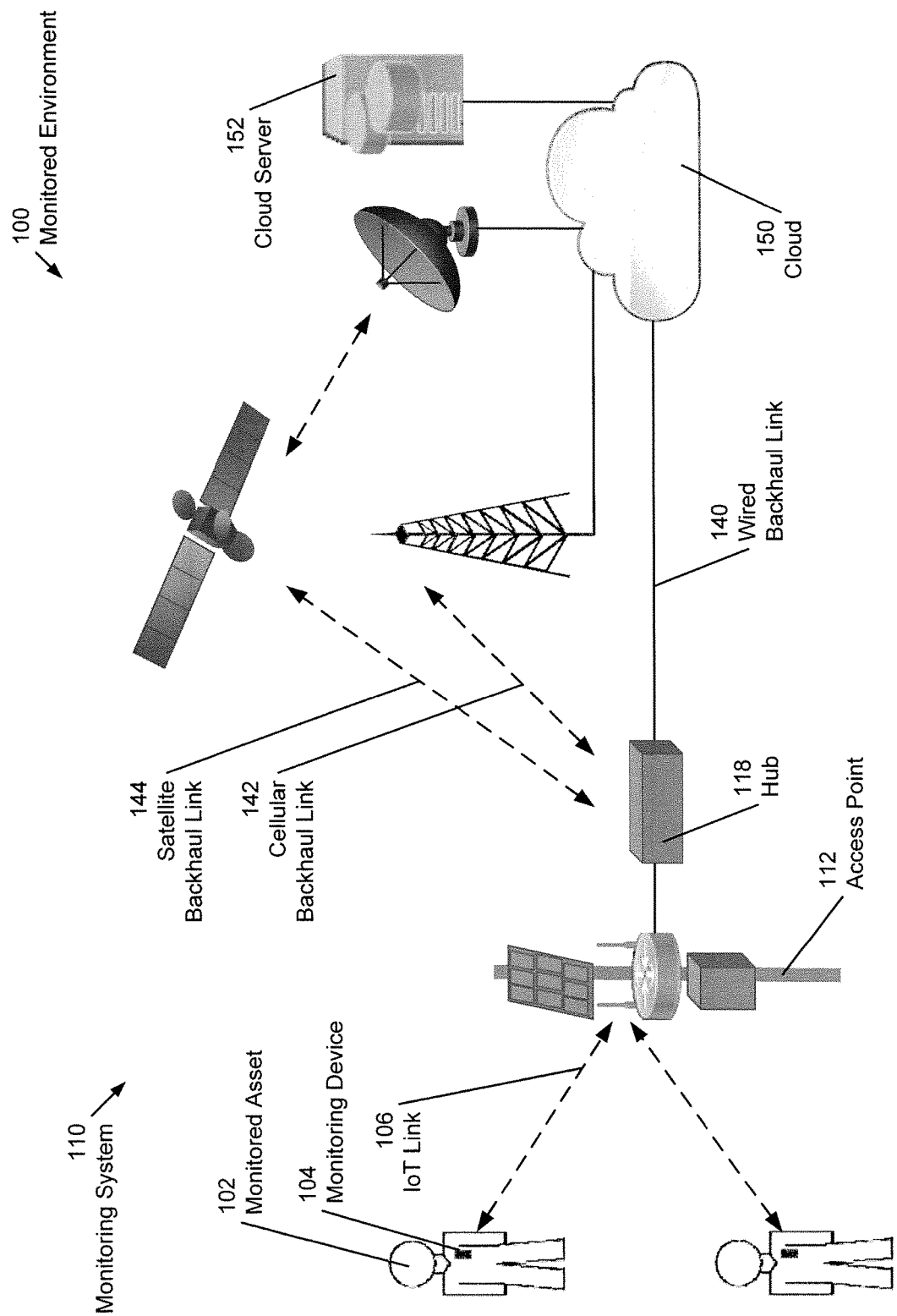

Turning to FIG. 1D, various options for interfacing the hub (118) with the computing devices in the cloud (150), e.g., using the Internet, are illustrated, in accordance with one or more embodiments of the invention. A wired backhaul uplink (140), a cellular backhaul uplink (142) and/or a satellite backhaul uplink may be used to interface the hub (118) with a cloud computing device, e.g., the cloud server (152). Alternatively, any other data connection, including any kind of point-to-point or multipoint connection that is at least temporarily available may be used as a backhaul link. In one embodiment of the invention, no backhaul link is used, i.e., the hub (118) is operating without an interface to the cloud (150), and therefore may only be accessed using local computing devices accessing the hub (118) via the access point (112), as previously described with reference to FIG. 1C. Alternatively, in one embodiment of the invention, no hub is used, i.e., the access point(s) may be directly connected to the backhaul link. Such a configuration may be suitable if the backhaul link is considered very reliable. Alternatively, if the backhaul link is considered less reliable, the hub may provide full or at least partial functionality while the cloud is not reachable.

The wired backhaul link (140) may be, for example, a wired Ethernet connection to an Internet service provider, a fiber-optic connection, a DSL Internet connection, a cable Internet connection, etc. Any type of wired data interface suitable to connect the hub to the cloud environment (150) may be used. The cellular backhaul link may be any type of cellular data connection such as a 3G, LTE or 5G data connection. Those skilled in the art will appreciate that any type of wired or wireless data link may be used as a backhaul link, without departing from the invention.

Figure 1E:
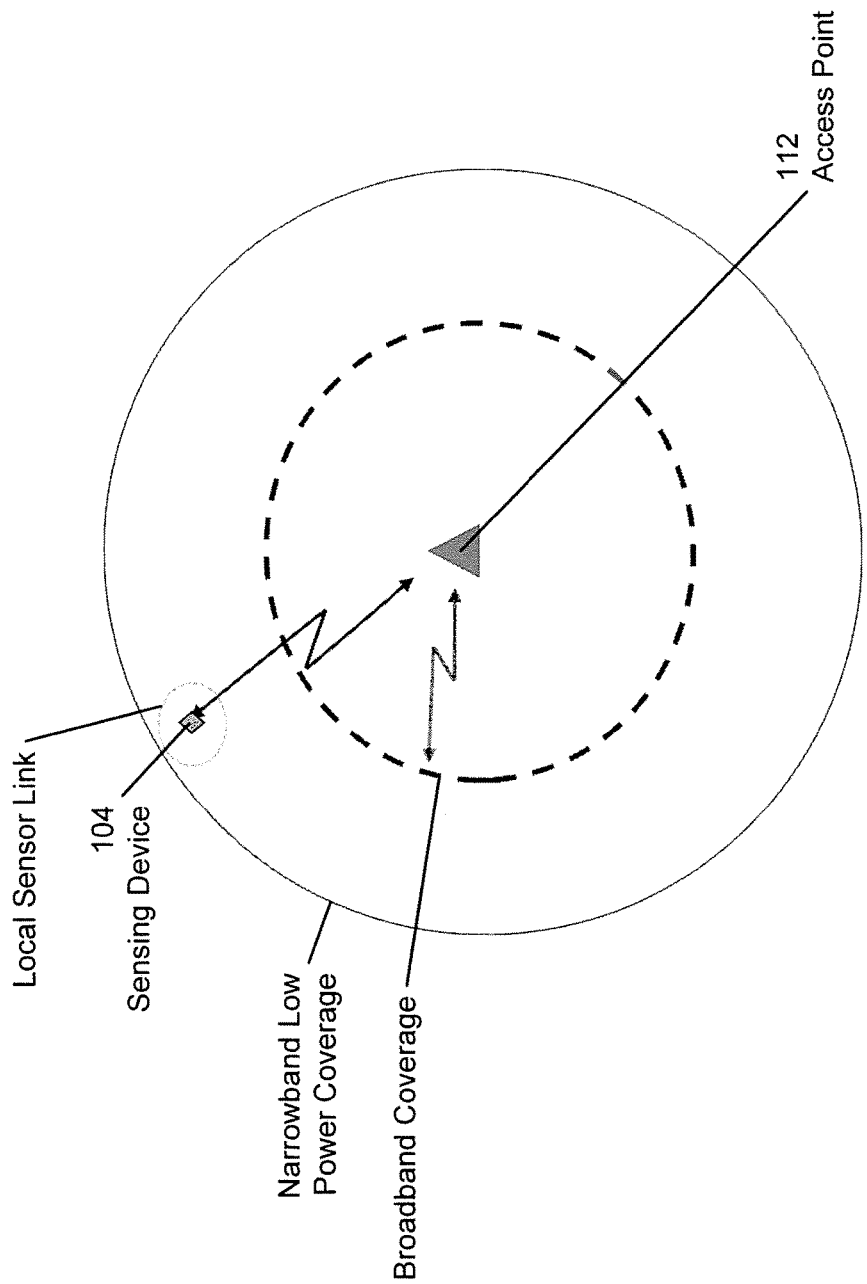

Turning to FIG. 1E, an exemplary radio signal coverage by a single access point (112), in accordance with one or more embodiments of the invention, is shown. As illustrated, a smaller region surrounding the access point receives broadband coverage (dashed circle), e.g., via the Wi-Fi signal of the access point. Within this zone, sensors that require a broadband link, e.g. cameras, may be installed. A larger region, surrounding the access point, receives narrowband coverage by the IoT link (108) (solid circle). While less data may be transmitted using the IoT link, data transmission using the IoT link may require less power and may be feasible over longer distances, in comparison to the broadband link. A monitoring device (104), which is typically battery-powered, therefore may use the IoT link rather than the broadband link. Those skilled in the art may appreciate that the areas that receive broadband and narrowband coverage depend on various factors, including the transmission power of the components involved in data transmissions, the types of antennas being used, terrain features, etc.

Figure 1F:
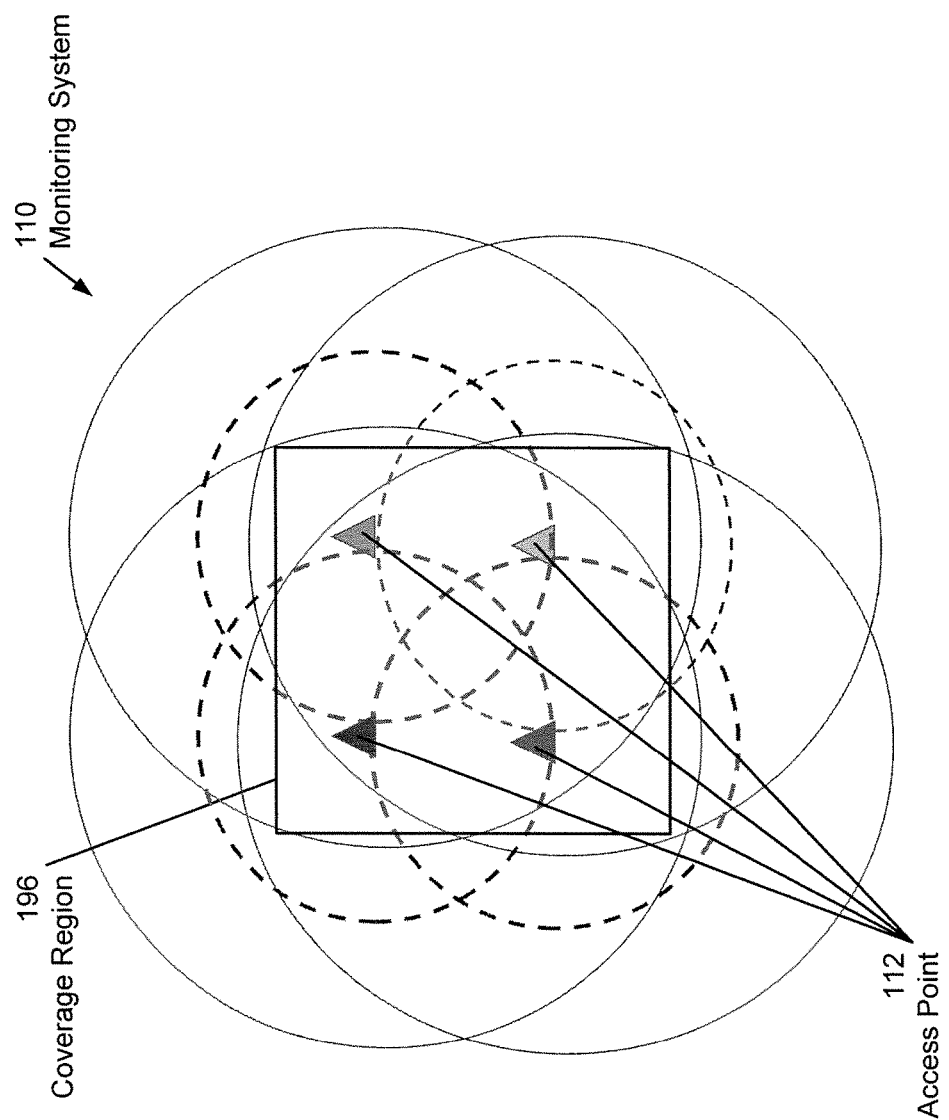

Turning to FIG. 1F, an exemplary radio signal coverage by multiple access points (112), in accordance with one or more embodiments of the invention, is shown. In the shown configuration, the access points are spaced such that there is significant overlap between the broadband coverage (dashed circles) provided by the different access points, but also between the narrowband coverage (solid circles) provided by the different access points. Using the set of access points, a coverage region (196) is entirely covered by narrowband signals of at least three access points. In one or more embodiments of the invention, overlap of narrowband coverage provided by multiple access points is desirable. Specifically, in a region where a sensor receives narrowband coverage by at least three narrowband signals (e.g., IoT signals), the signals of a monitoring device, received by at least three access points may be used to determine the location of the monitoring device, thus enabling, for example, location tracking of a monitored asset (102) equipped with a monitoring device (104). The location of a monitoring device may be determined using time difference of arrival (TDOA) methods. Accordingly, location tracking using TDOA methods may be performed in the coverage region (196) in which at least three access points may receive transmissions sent by the monitoring device. TDOA positioning may provide moderately accurate location information (e.g. with an accuracy of approximately 30-75 m), although the accuracy may deteriorate when the quality of the reception at one or more of the access points is poor. The measurement accuracy may, however, not be strongly affected by the presence of buildings and foliage. Alternatively, received signal strength indication (RSSI) positioning may provide location information with limited accuracy, (frequently no more accurate than approximately 75 m), and may allow positioning even under difficult conditions, e.g., when fewer than three access points are available. Further, if equipped with a global positioning system (GPS) receiver, the monitoring device's location may be determined using the GPS receiver. GPS positioning does not rely on the exchange of signals with access points and may thus be available anywhere, even outside the coverage region (196), although power requirements may be significantly higher when relying on GPS. Further, GPS signals may be blocked by structures, foliage, etc. However, the accuracy is typically higher than the accuracy of the TDOA and RSSI methods.

Accordingly, to enable energy efficient location determination in certain regions, access points may be strategically placed to have overlapping coverage regions, thereby not requiring the use of power consuming GPS positioning. In regions where TDOA based location services are desired, a dense grid of access points with a high degree of overlap may be installed to ensure that overlapping coverage is provided by at least three access points, whereas a sparse grid of access points may be installed in other regions. In these other regions, less accurate RSSI positioning may be used, or if an accurate location is required, GPS positioning may be used.

Figure 1G:
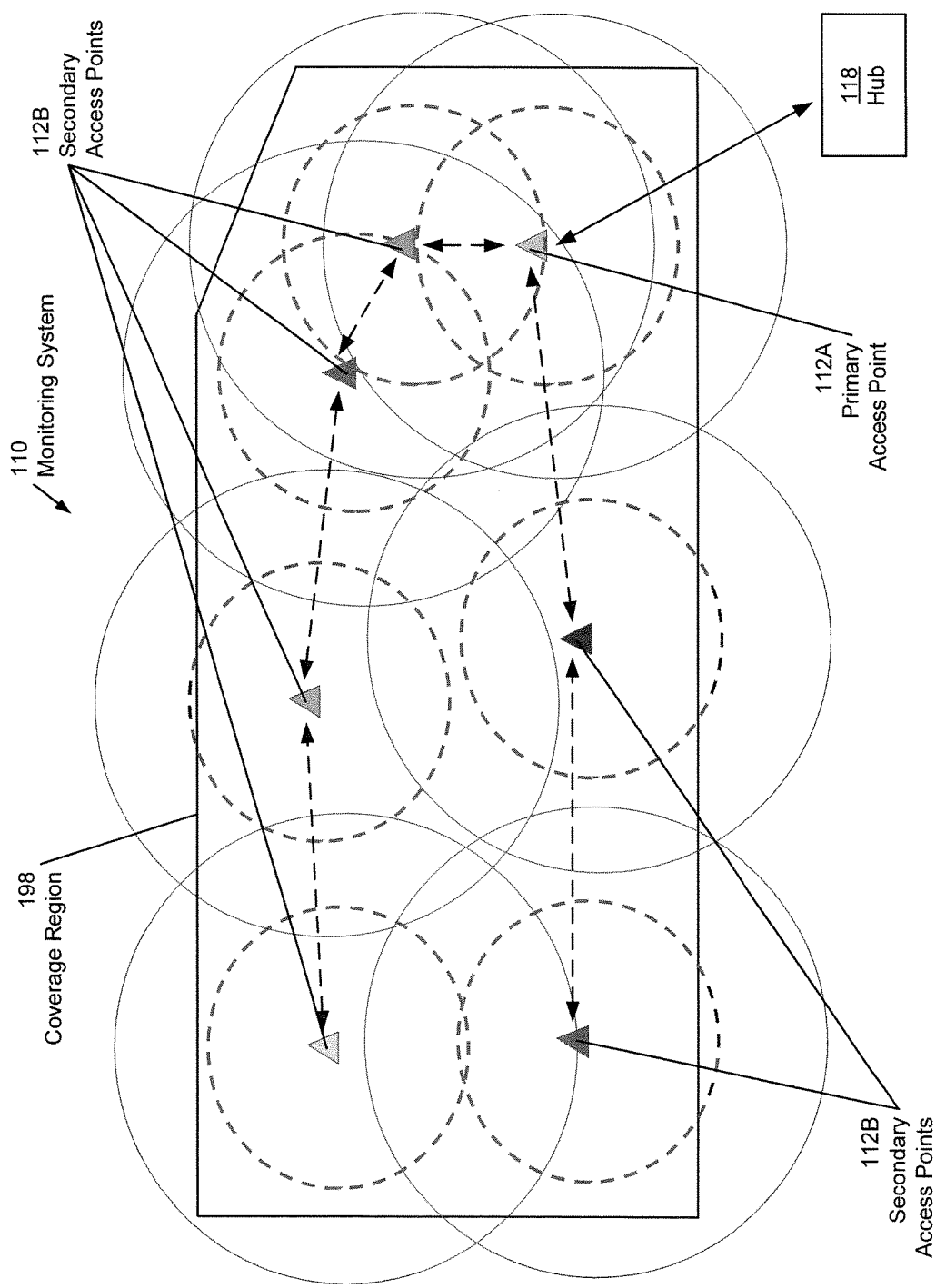

Turning to FIG. 1G, an exemplary radio signal coverage by multiple access points (112A, 112B), in accordance with one or more embodiments of the invention, is shown. To cover large areas effectively while allowing for extended battery life, up to years, access points may need to be deployed strategically to cover the desired monitored environment. The configuration shown in FIG. 1G uses a primary access point (112A) that directly interfaces with a hub (118) and provides an interface to the secondary access points (112B). Using the set of access points, a coverage region (198) is entirely covered by a narrowband signal (solid circles), while some areas are also covered by a broadband signal (dashed circles). In the exemplary configuration shown in FIG. 1G, the left part of the coverage region (198) is covered by sparsely placed access points, where broadband coverage regions are non-overlapping. In contrast, the right part of the coverage region (198) is covered by densely placed access points, where broadband coverage is overlapping, thus establishing a contiguous region with broadband signal coverage. Those areas may, thus, serve different purposes. For example, the left part may be used to monitor sensors that merely require a narrowband communication interface, e.g., weather sensors or monitoring devices for assets that do not require TDOA tracking. In contrast, the right part may be used for a drone surveillance that requires a continuous broadband signal. Those skilled in the art will appreciate that even though FIG. 1G shows the primary access point (112A) interfacing with a hub (118), the hub is not necessarily required. For example, the primary access point (112A) may directly interface with the cloud environment (150). Further, to provide coverage for larger areas and/or for larger numbers of assets to be tracked, additional access points, including primary and/or secondary access points and/or additional hubs may be deployed.

Figure 1H:
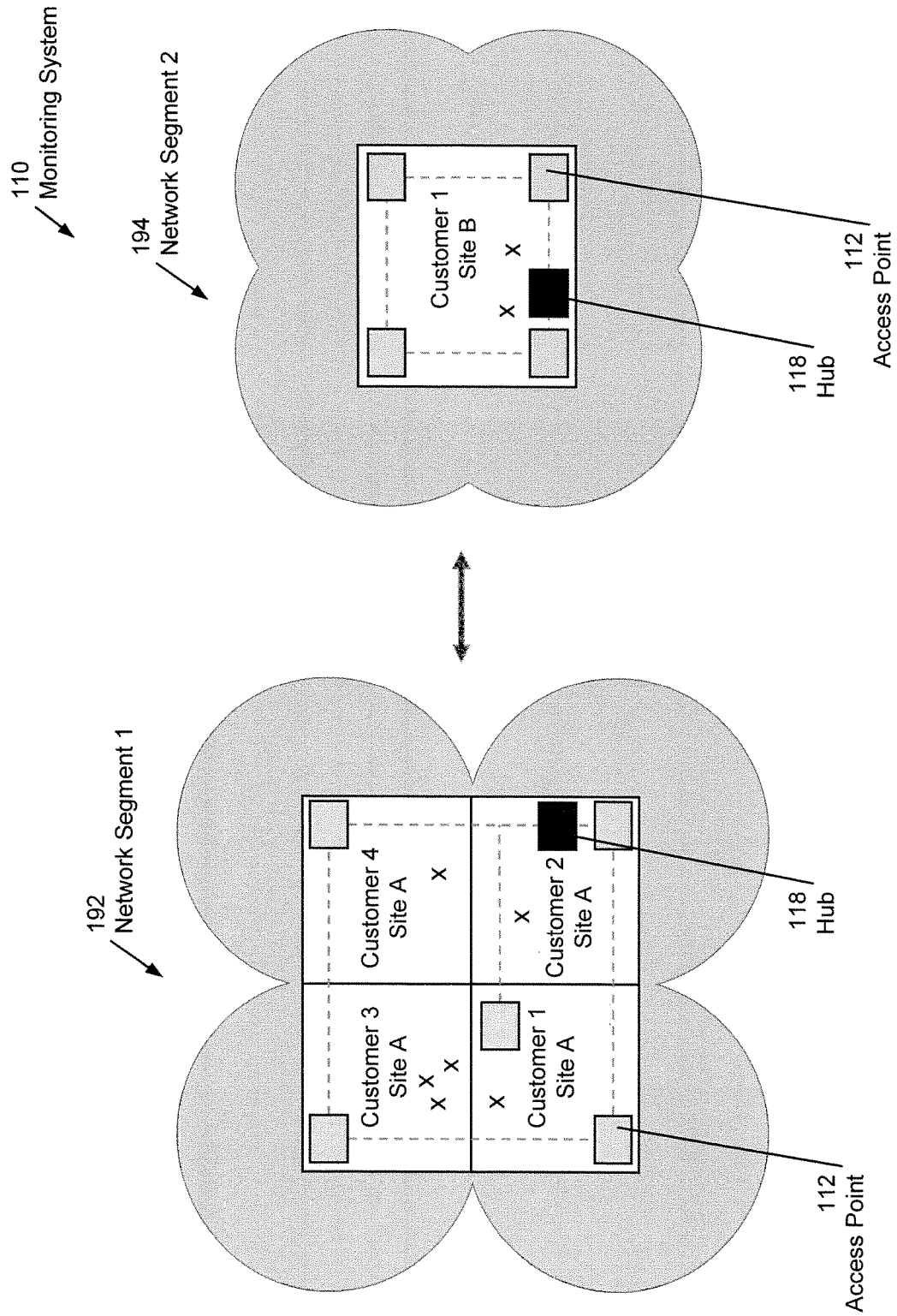

Turning to FIG. 1H, an exemplary monitoring system (110) that includes multiple network segments (192, 194), in accordance with one or more embodiments of the invention, is shown. Each of the network segments (192, 194), is equipped with a hub (118) and multiple access points (112), providing monitoring coverage. Alternatively, these network segments may be operated without hubs. Further, both network segments operate using the same RF plan, i.e., using the same transmission protocol and frequencies, further described in FIG. 6. Network segment 1 (192) is configured as a multitenant site, i.e., multiple customers (customers 1-4, site A) are served by the network segment. Consider, for example, a monitoring system (110) that is installed in a healthcare facility that is shared by multiple care providers. Assume that these care providers have in common that their patients require monitoring. Accordingly, the care providers agree to have a common monitoring system installed by a monitoring service provider that offers the monitoring as a service. Customer 1 is an assisted living provider with patients that may suffer from dementia and may therefore get disoriented within their environment. Staff therefore needs to be able to locate these patients. Customer 2 is a nursing home provider with patients that temporarily need support and may spontaneously need assistance, thus requiring localization of patients whenever they need assistance. Customer 3 is a mental health care center. Patients may be violent or may attempt to escape and therefore need to be monitored as well. Customer 4 is a drug rehabilitation center, where patients may also be violent and may try to escape and therefore also need to be monitored. Patients of the assisted living facility and the nursing home facility may be allowed to freely move between the assisted living facility and the nursing home facility. In contrast, allowed movement of patients of the mental health center and the drug rehabilitation center is strictly limited to areas within their respective facilities. The assisted living provider further operates a second assisted living facility on site B that is separate from site A, and that is covered by network segment 2 (194). Because network segments 1 and 2 belong to the same monitoring system, information about devices may be exchanged between the network segments. Accordingly, moving patients between site A and site B is straightforward. The scenario of FIG. 1H thus illustrates a multi-tenant, multisite monitoring system, in accordance with one or more embodiments of the invention. Those skilled in the art will appreciate that monitoring systems, in accordance with one or more embodiments of the invention, are fully scalable. For example, monitoring systems may include any number of sites, any number of customers and any number of patients or, generally speaking, assets to be monitored. Further, monitoring systems, in accordance with one or more embodiments of the invention, may be globally distributed. For example, sites A and B may be on different continents. Network segments may grow arbitrarily large, with any number of access points and/or monitoring devices. However, eventually a network segment with numerous devices may become congested, or the hub of the network segment may be overwhelmed by the incoming volume of data. In such a scenario, the network segment may be split into two or more separate network segments, each with its own hub and access points.

Figure 2A:
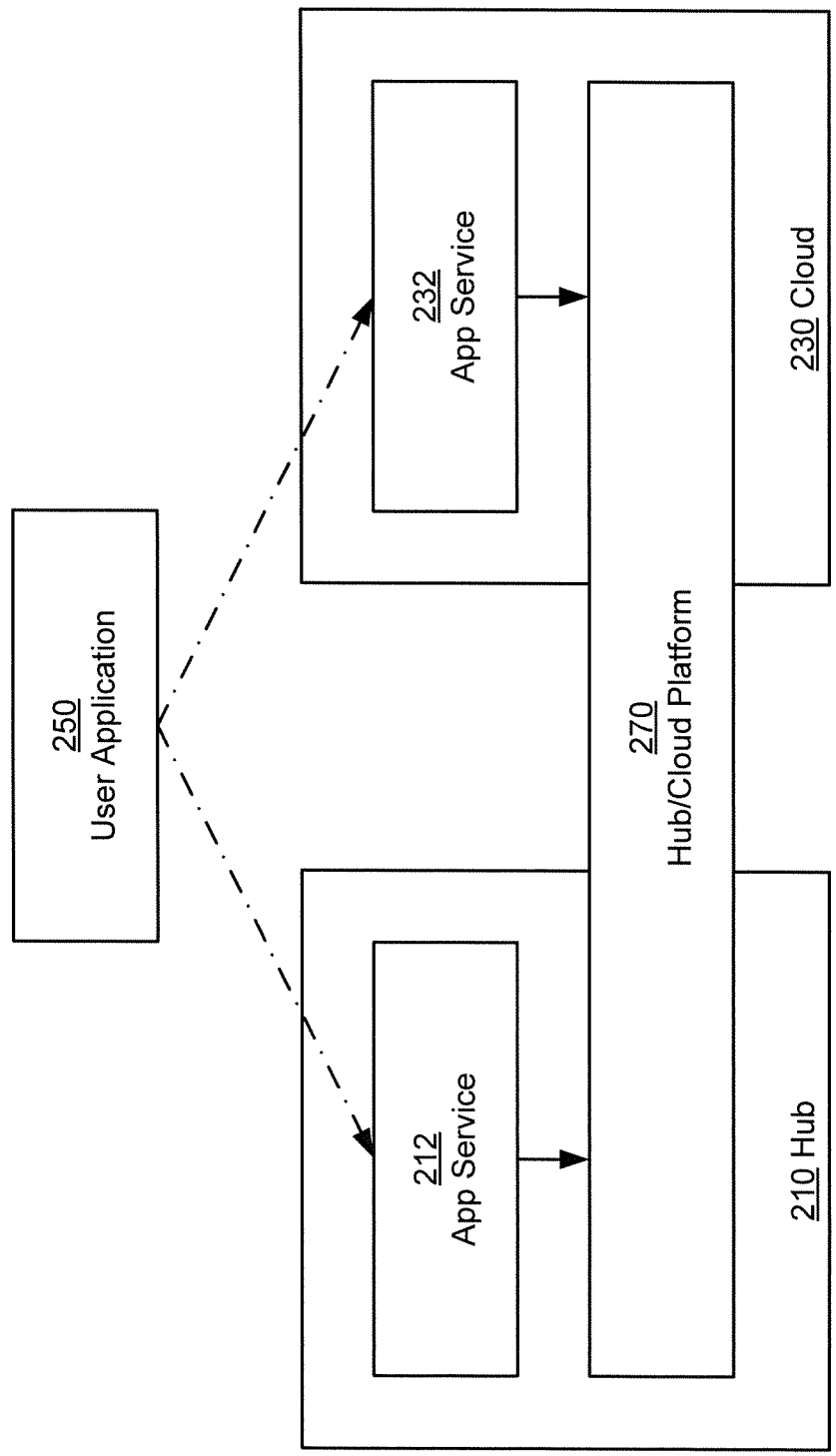
FIGS. 2A and 2B show a hub-cloud configuration of a system for monitoring assets, in accordance with one or more embodiments of the invention.

Turning to FIG. 2A, a hub-cloud configuration of a system for monitoring assets, in accordance with one or more embodiments of the invention, is shown. The hub-cloud configuration includes the hub (210), the cloud (230), and the user application (250). A hub/cloud platform (270), jointly executing on the hub (270) and in the cloud (230) in a distributed manner, provides back end-support for various components of the monitoring system (110), as further described with reference to FIG. 2B. A user application (250) may be relied upon by a user to access the hub/cloud platform (270) via the hub (210) and/or via the cloud (230). Each of these components is subsequently described.

Services, made available through the hub/cloud platform (270) may include, for example, providing data, gathered by the monitoring system (110), to the user, enabling the user to configure the monitoring system, etc. The hub/cloud platform (270) may be accessed by a user using the user application (250), which may be executing on a computing device such as a smartphone or a laptop. The user application (250), thus, may provide a user interface configured to enable the user to access the hub/cloud platform, and to receive notifications on critical events. The user application may include for example, alert displays, status messages, data visualization capabilities, control and configuration capabilities, etc. The user application may further provide data entry fields (e.g., to configure the monitoring system), specialized control interfaces (e.g., to control a drone), voice over IP (VoIP) and/or push to talk interfaces and other communication interfaces that are supported by the broadband links provided by the access points. Alternative implementations of the user application (250) may operate on other devices, e.g., on an audio alert device.

Depending on whether the user application (250) accesses the hub/cloud platform (270) via the hub (210) or via the cloud (230), the user application (250) may interface with the hub/cloud platform via the app service (212) of the hub (210) (e.g., using a smartphone's Wi-Fi interface) or via the app service (232) of the cloud (230) (e.g., using the smartphone's LTE interface). When a user is on-site, e.g., directly connected to an access point using a Wi-Fi link, accessing the hub/cloud platform (270) may be particularly low-latency because the interaction of the user's computing device with the hub is local.

The hub (210) includes a computing device configured to perform at least some of the steps described with reference to the flowchart of FIG. 8, and one or more communication interfaces that enable the hub to interface with one or more access points (112), the cloud (230), and the computing device that executes the user application (250). The computing device of the hub may be, for example, an embedded system that includes all components of the computing device on a single printed circuit board (PCB), or a system on a chip (SOC), i.e., an integrated circuit (IC) that integrates all components of the computing device into a single chip. The computing device may include one or more processor cores, associated memory (e.g., random access memory (RAM), cache memory, flash memory, etc.), one or more network interfaces (e.g., an Ethernet interface, a Wi-Fi interface, a Bluetooth interface, etc.), and interfaces to storage devices, input and output devices, etc. The computing device may further include one or more storage device(s) (e.g., a hard disk, an optical drive such as a compact disk (CD) drive or digital versatile disk (DVD) drive, flash memory, etc.), and numerous other elements and functionalities. In one embodiment of the invention, the computing device includes an operating system that may include functionality to execute the methods further described below. Those skilled in the art will appreciate that the invention is not limited to the aforementioned configuration of the computing device.

Figure 7:
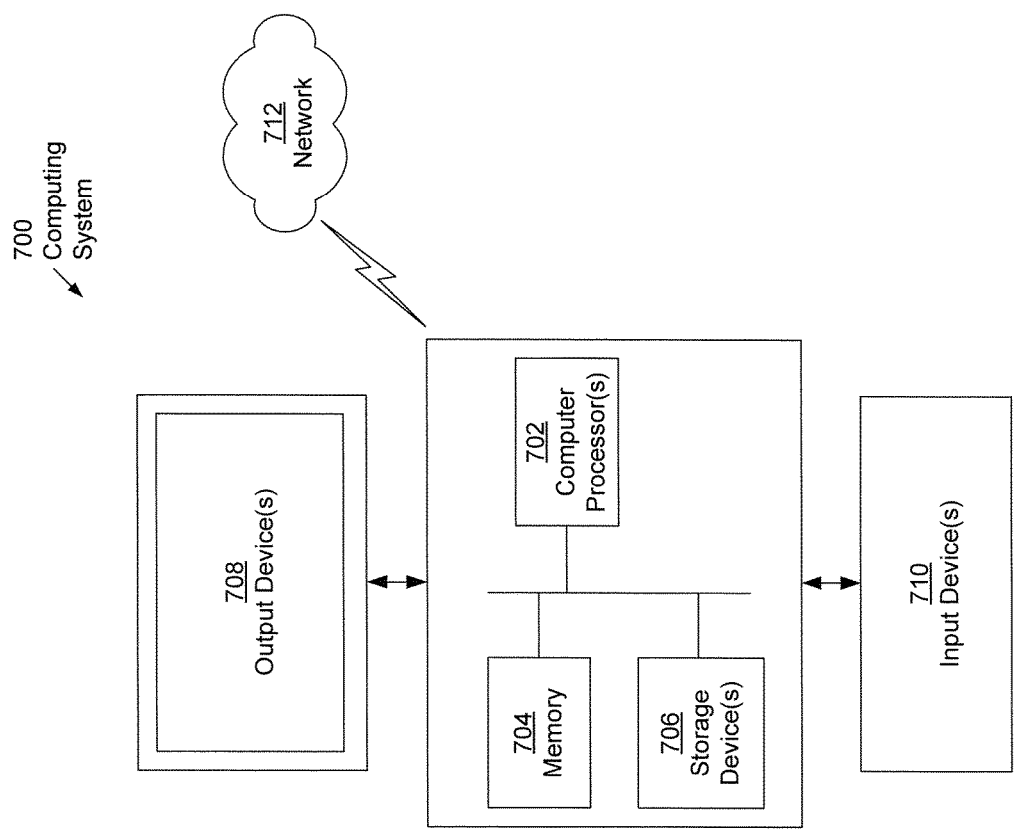
FIG. 7 shows a computing system in accordance with one or more embodiments of the invention.

The cloud (230), in accordance with one or more embodiments of the invention, may be formed by multiple/many networked computing devices. These computing devices may be geographically and organizationally distributed in any way. For example, some of these computing devices may be located in a data center, whereas other such computing devices may be individual physical or virtual servers. An exemplary computing system, as it may be used in the cloud, is shown in FIG. 7. One or more of the computing devices may host the hub/cloud platform (270), analogous to how the hub/cloud platform is hosted on the hub (210). While the components of the hub/cloud platform that are executing on the hub (210) and that are executing on a computing device in the cloud (230) may operate separately, they are interconnected, e.g. via the backhaul link (140), thus enabling synchronization between these components. Accordingly, the same information may be available, regardless of whether the user application connects via the hub (210) or via the cloud (230). Temporary discrepancies may exist though, e.g., during times when the backhaul link (140) is interrupted, and a synchronization is therefore unavailable. Further, because additional, e.g., more complex, data processing may be performed in the cloud, additional data, resulting from the additional processing, may be available when connecting to the hub/cloud platform (270) via the cloud. Such data may, however, also be available via the hub (210), if they are synchronized to the hub (210) via the backhaul link (140). The cloud may run multiple instances of the hub/cloud platform in order to support the load of many sites and/or many users. Depending on the configuration of the hub/cloud platform, incoming data, i.e., data received from a particular hub, a particular device, a particular site, or a particular customer, may be distributed between multiple instances, or may be consistently assigned to the same instance, using, e.g., a consistent hash ring configuration.

Those skilled in the art will recognize that other configurations that deviate from the configuration introduced in FIG. 2A may exist, without departing from the invention. For example, in monitoring systems (110) that do not include an interface to the cloud (230), the hub/cloud platform (270) may solely execute on the hub. In such a scenario, the hub is configured to "self-backhaul", i.e., the hub may collect and consolidate monitoring device data and may perform some or even all of the processing that would otherwise be performed in the cloud. Similarly, in monitoring systems in which the access points (112) directly interface with the cloud (230), the hub/cloud platform (270) may solely execute in the cloud. All functionality, even functionally that would typically be provided by the hub, in this case may be provided in the cloud. The configuration of the monitoring system, with or without hub, in one or more embodiments of the invention, may be transparent, i.e., monitoring devices or other devices may operate in the same manner, regardless of the presence of a hub. Similarly, a user may experience the same monitoring system, whether the hub is present or not.

Figure 2B:
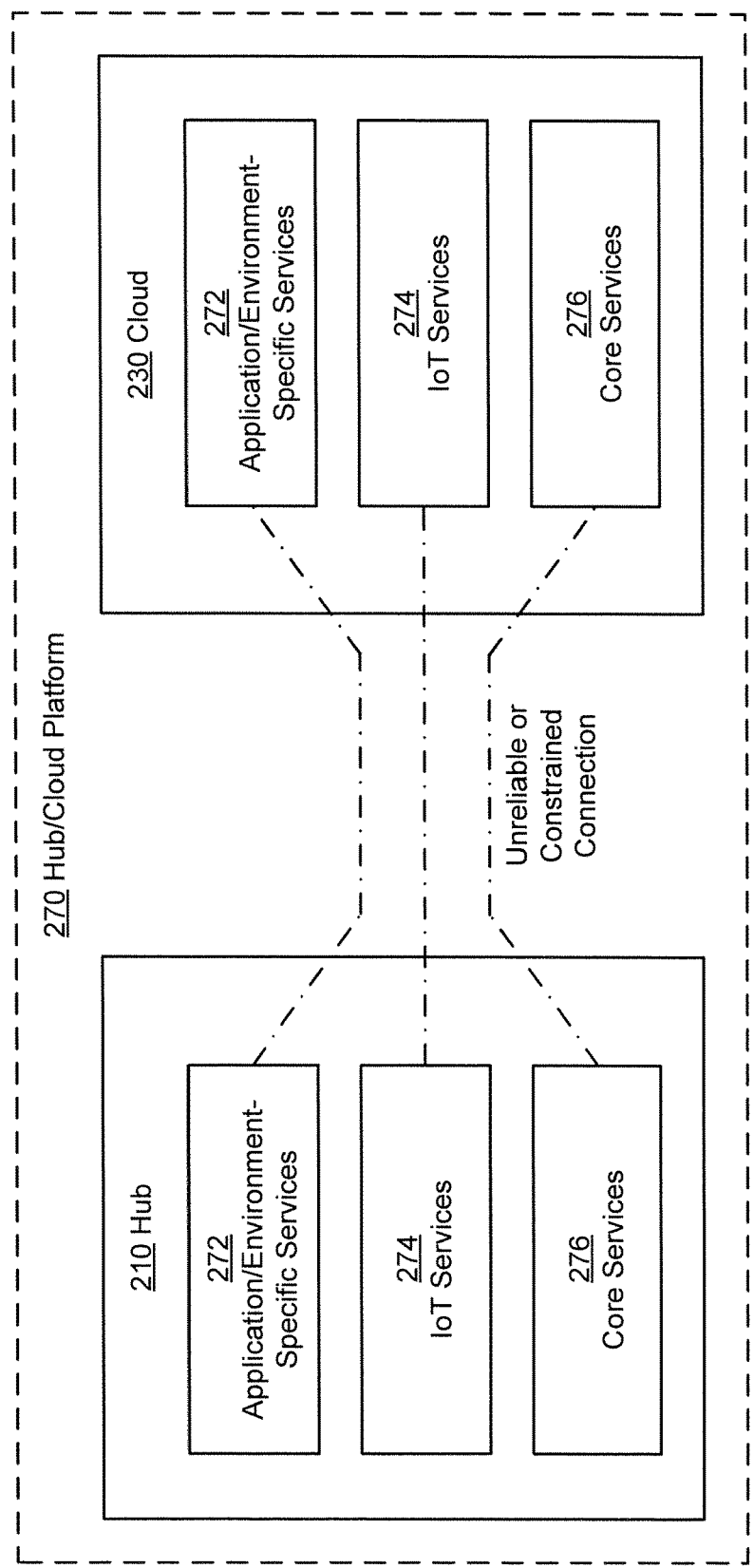

Turning to FIG. 2B, additional details of the hub/cloud platform (270) are shown. In one or more embodiments of the invention, the hub-cloud platform is organized in layers. Core services (276) provide basic functionalities such as data storage, network, and messaging. On top of the core services (276), the IoT services (274) provide services that are specific to IoT networks, but that are not necessarily specific to a particular application, such as the use in a healthcare environment. The IoT services may thus include, for example, location services (e.g., GPS, TDOA or RSSI based), IoT network services and configurations, etc. The topmost layer includes application and/or environment-specific services (272). These services, in case of a healthcare environment may include, for example, analysis of patients' vital signs, a patient location tracking interface, etc. In contrast, in case of an oilfield environment, these services may include, pipeline operation analytics. Additional application-specific layers may be added, without departing from the invention. The hub/cloud platform is, thus, modular, allowing adaptation to many applications, depending on the services selected for execution on the hub/cloud platform.

These services, in accordance with one or more embodiments of the invention, may be available through the hub (210) and/or through the cloud (230). A synchronization may be performed between the services executing in the cloud and the services executing on the hub, thus maintaining consistency between the hub and the cloud. As long as a communication link (e.g., the backhaul link (140)) is available, the data available through the hub and through the cloud may be identical. However, if the communication link temporarily becomes unavailable, data that is accumulated on the hub may not be available through the cloud. A synchronization may be performed once the communication link is restored, to update the cloud with the data available on the hub. Accordingly, a consistent data view is available via hub and cloud, in accordance with one or more embodiments of the invention.

Figure 3B:
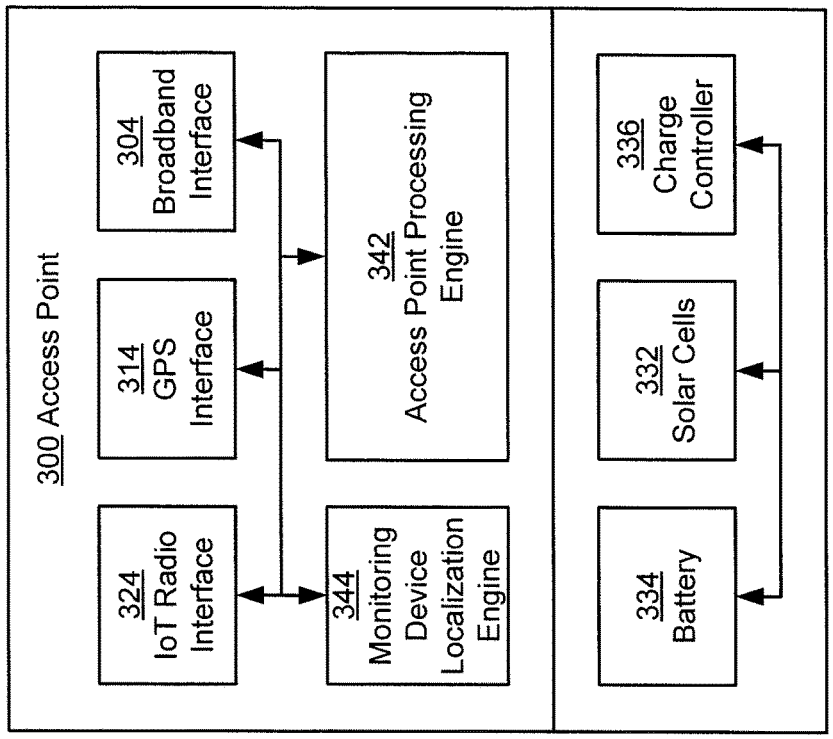
Figure 3A:
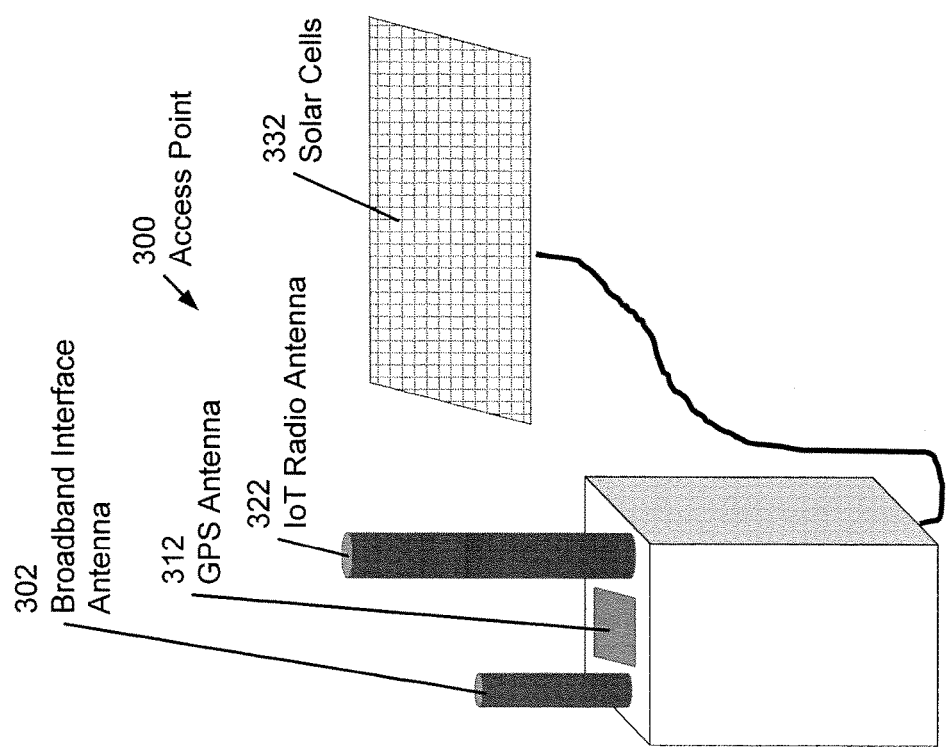
Figure 3E:
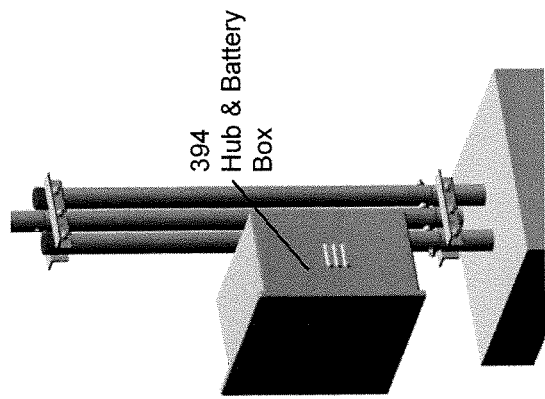
Figure 3D:
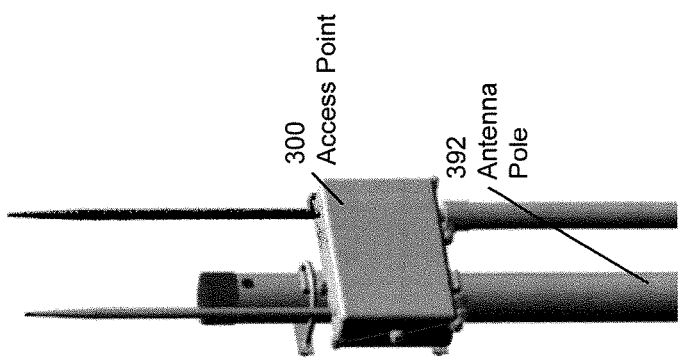
Figure 3C:
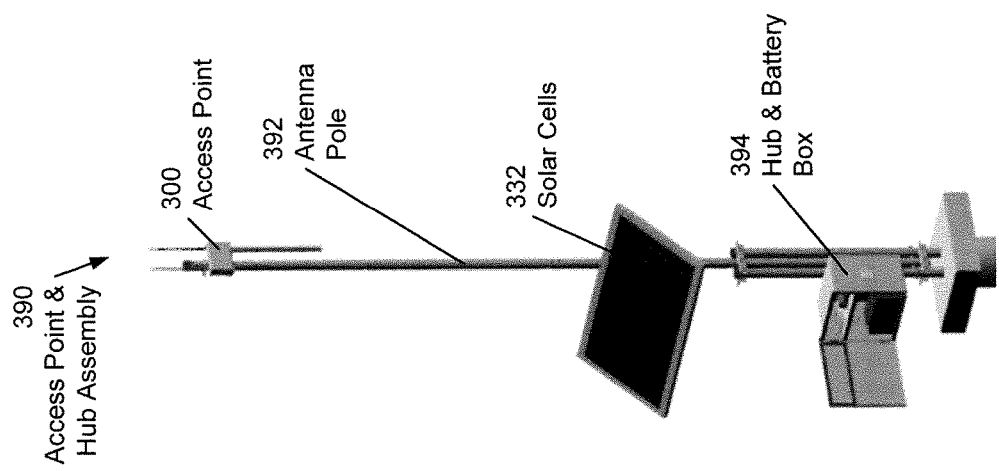

Turning to FIGS. 3A and 3B, access points (300), in accordance with one or more embodiments of the invention, are shown. In FIG. 3A, the general design of an exemplary access point is shown, and in FIG. 3B, the architecture of the access point is illustrated. The exemplary access point shown in FIG. 3A includes a broadband interface antenna (302), a GPS antenna (312), an IoT radio antenna (322) and solar cells (332). As shown in FIG. 3B, the access point further includes a broadband interface (304), a GPS interface (314) and an IoT radio interface (324).

The broadband interface (304) uses the broadband antenna (302) in order to send and receive broadband data transmissions when in contact with, e.g., other access points, as illustrated in FIG. 1B and/or with other devices such as smartphones, laptops, cameras and/or drones that are also equipped with broadband interfaces. The broadband interface may support mesh, point-to-point and multi-point connections. The broadband interface may be based on the Wi-Fi standard, using, e.g., the 2.4 and/or 5 GHz radio bands. Alternatively, the broadband interface may be a cellular data interface, e.g., a 3G or 4G/LTE or 5G interface, or any other wireless data interface, without departing from the invention.

The GPS interface (314) uses the GPS antenna (312) to obtain position signals from the global positioning system or from alternative satellite navigation services. The position signal enables the access point to accurately determine its own position. In one or more embodiments of the invention, the GPS interface further obtains an accurate time base that may be used by the access point to perform localization tasks using TDOA methods, as further described below.

The IoT radio interface (324) uses the IoT radio antenna (322) to communicate with one or more IoT devices such as the monitoring devices (104). The IoT interface may be based on a low power wide area network standard such as, for example, LoRa. The resulting narrowband link is particularly suitable for communications between the access point and the monitoring devices or other sensors, due to its low power requirements, long range, and its ability to interface with many monitoring devices and/or other devices. In one or more embodiments of the invention, the IoT radio interface (324) supports communication protocol extensions implemented on top of an existing IoT communication protocol to provide scheduled communications and timing beacons as further discussed below, with reference to FIG. 6.

In one or more embodiments of the invention, the access point (300) further includes an access point processing engine (342). The access point processing engine may handle the processing of data received from monitoring devices and other sensors, and may coordinate the uploading of the processed data to either the hub or to the cloud. The processing of data may involve, for example, data aggregation, data filtering, data fusion, data compression and/or data encryption.

Figure 6:
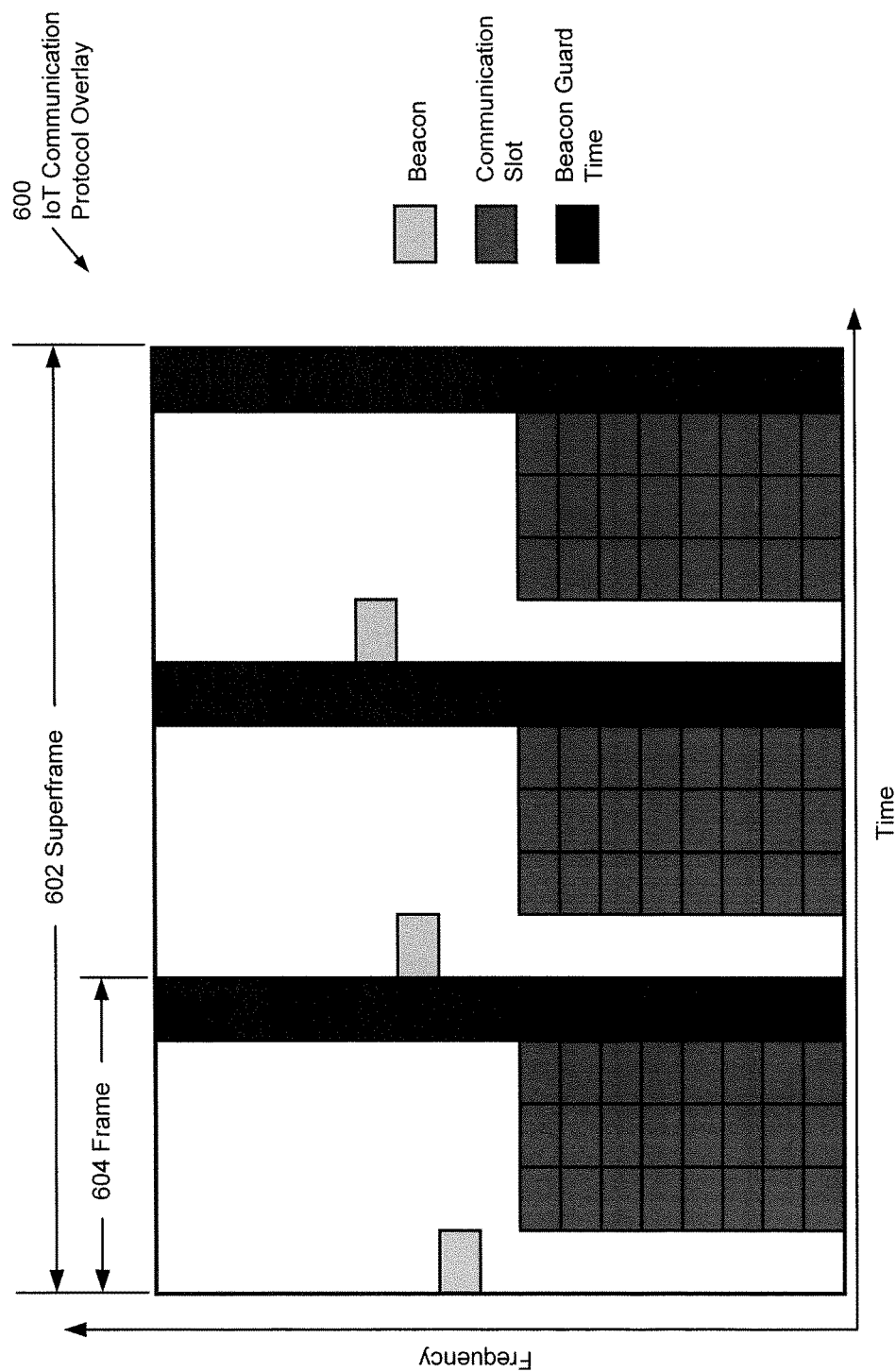
FIG. 6 shows an Internet of Things (IoT) communication protocol overlay, in accordance with one or more embodiments of the invention.

In one or more embodiments of the invention, the access point (300) further includes a monitoring device localization engine (344). The monitoring device localization engine may be used to determine the locations of monitoring devices that are within the coverage region of the access point. The localization may be performed, for example, using TDOA methods. Using the TDOA method, triangulation, based on the differences in time delay of a data transmission by a monitoring device, received by at least three access points, may be performed. The monitoring device localization engine of an access point may use this time delay information to determine the location of the monitoring device responsible for the data transmission. Because TDOA methods depend on the availability of an accurate time base to the monitoring devices whose location is to be determined, communication protocol extensions that enable dissemination of an accurate time base to the monitoring devices via the IoT link, as discussed with reference to FIG. 6, are used by the access point. Alternatively, the monitoring device localization engine may extract the location of a monitoring device from a message provided by a sensor equipped with a GPS unit. Further, the monitoring device localization engine may also determine a location of a monitoring device based on the signal strength of a data transmission obtained from the monitoring device, using the RSSI method. Those skilled in the art will appreciate that, although the method performed by the monitoring device localization engine is described with regard to monitoring devices, any device that is equipped with an IoT interface, and that is capable to communicate with the access points, may be localized by the monitoring device localization engine.

The access point processing engine (342) and the monitoring device localization engine (344) may be software executing on a computing device (not shown) of the access point (300). The computing device of the hub may be, for example, an embedded system that includes all components of the computing device on a single printed circuit board (PCB), or a system on a chip (SOC), i.e., an integrated circuit (IC) that integrates all components of the computing device into a single chip. The computing device may include one or more processor cores, associated memory (e.g., random access memory (RAM), cache memory, flash memory, etc.), and interfaces to storage devices, input and output devices, etc. The computing device may further include one or more storage device(s) (e.g., a hard disk, an optical drive such as a compact disk (CD) drive or digital versatile disk (DVD) drive, flash memory, etc.), and numerous other elements and functionalities. In one embodiment of the invention, the computing device includes an operating system that may include functionality to execute the methods further described below. Those skilled in the art will appreciate that the invention is not limited to the aforementioned configuration of the computing device.

In one or more embodiments of the invention, the access point further includes a power system that may include the solar cells (332), a battery (334) and a charge controller (336), powering the access point. The battery may be deep-cycle capable to guarantee continued operation at night or under cloudy conditions when power provided by the solar cells is insufficient. The solar cells may be dimensioned to enable powering the access point while also recharging the battery. Alternatively, the access point may be powered externally, e.g., using power over Ethernet (PoE) or using a dedicated power input. The charge controller in combination with the access point processing engine (342) may provide charging, battery status and power consumption analytics, enabling power management of the access point. A direct current (DC) power and data over DC power link may be used to power the access point by the power system, but also to enable the charge controller to communicate status information (such as battery level, temperature, etc.) to the access point.

FIGS. 3C-3G show an exemplary access point & hub assembly, in which a hub and an access point are installed in combination on a pole. The assembly (390) includes the access point (300), an antenna pole (392), solar cells (332) and a hub & battery box (394). Alternatively, the access point & hub assembly may be powered by AC line voltage, either continuously or intermittently. In this case, the access point & hub assembly may not be equipped with solar cells, but may instead include AC to DC conversion circuits to power the access point & hub assembly and/or to charge the battery. While the access point (300) is installed near the top of the antenna pole (392), for improved reception, the hub (318) may be housed in the hub & battery box (394), together with the battery (334) and the charge controller (336) near the base of the antenna pole (392), thus facilitating access. The access point (300) may be connected to the hub (318), using an Ethernet cable, which may also power the access point using PoE. In one embodiment of the invention, the antenna pole (392) can be pivoted into a horizontal position, thereby facilitating installation and servicing of the access point (300) near the top of the antenna pole as illustrated in FIG. 3G

Figure 4:
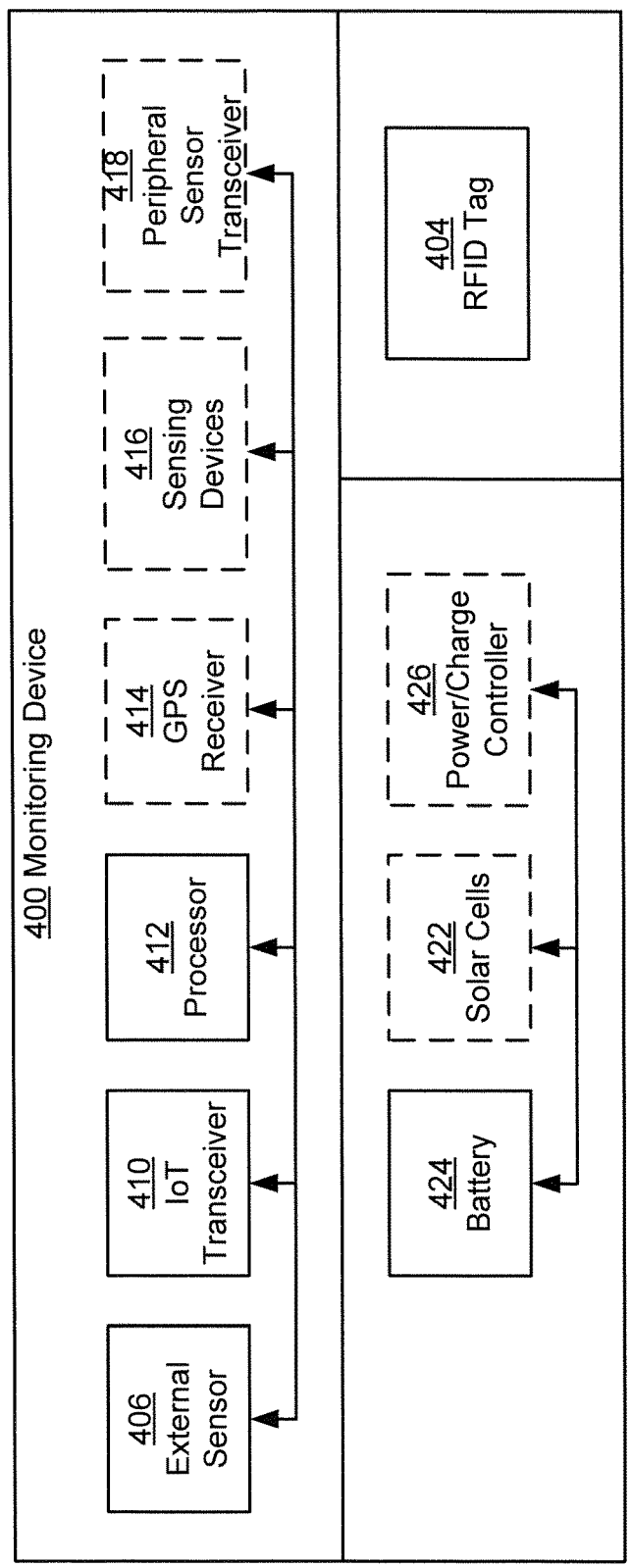
FIG. 4 shows a monitoring device of a system for monitoring assets, in accordance with one or more embodiments of the invention.

FIG. 4 shows a monitoring device (400) in accordance with one or more embodiments of the invention. A monitoring device may be used to monitor an asset, including the asset's location and other variables, as subsequently discussed. The monitoring device may be equipped with a mounting or attachment element that is application specific. For example, in industrial or commercial applications, the monitoring device may be permanently bolted to an equipment to be monitored. In animal applications, the monitoring device may be attached using an ear pin or a collar. Further, in human applications, the monitoring device may be designed as a wristband, an ankle monitor or as a unit that can be worn in a pocket. The monitoring device may further be installed on a hard hat, as it may be worn by workers in the oil & gas, construction, refining, and other industries. In such applications, the monitoring device may be a tag that is attached to the front or the back of a hard hat. In automotive applications, the monitoring device may be a tag that is hanging from the rear view mirror. If monitoring devices are used to track the location, temperature and/or fill level of portable tanks, such as propane tanks, these monitoring devices may be equipped with mounts to permanently or temporarily attach the monitoring devices to these tanks. Those skilled in the art will appreciate that the monitoring device is suitable for many applications and may thus be adapted to include mounting elements as needed. The monitoring device may further be equipped with an RFID tag. The RFID tag may electronically store information such as a unique asset-specific identifier. The RFID tag may be passive, i.e., not requiring a battery, and may be electromagnetically powered by a nearby reader, e.g., the RFID wand (132), previously discussed in FIG. 1C. The monitoring device may further include active components, including one or more external sensors (406). Data from these sensors may be transmitted to one or more of the previously introduced access points using the IoT link. The external sensors may be physiological sensors (e.g., blood pressure or heart rate sensors) or sensors for environmental variables such as temperature, humidity, etc. These sensors may have a wired or optical interface (e.g., infrared) to the monitoring device.

In one or more embodiments of the invention, the monitoring device (400) includes an IoT transceiver (410). The IoT transceiver (410) may be configured to communicate with one or more access points, using an IoT protocol such as LoRa. Communications may include, but are not limited to, the receiving of a time base from one or more access points, the receiving of a configuration, the receiving of a firmware, the sending of monitoring device data, e.g., data previously collected by one of the subsequently described sensors, and/or the sending of monitoring device status data, such as errors, battery level, etc. The activity of the IoT transceiver may be optimized to minimize power consumption. For example, the IoT transceiver may be in a deep sleep mode whenever no transmission of data is required.

In one or more embodiments of the invention, the monitoring device (400) further includes a processor (412). The processor may gather data from one or more of the subsequently described sensors and may process the data for transmission via the IoT transceiver. The transmissions may be performed as specified by the IoT communication protocol overlay, further described with reference to FIG. 6 to minimize communication inefficiencies such as collisions with data sent by other monitoring devices and/or to conserve battery power. The organization of the data as instructed by the IoT communication protocol overlay may be performed by the processor (412). The processor may be a microcontroller unit (MCU) that may be implemented as a system on a chip (SOC). The processor may be selected based on computational requirements and battery life requirements.

In one embodiment of the invention, the monitoring device (400) may include a GPS receiver (414), sensing devices (416) and/or a peripheral sensor transceiver (418). The GPS receiver, if present, may be used to determine the location of the asset when other, more power efficient, methods for determining the location (such as TDOA and/or RSSI) are not available, e.g., when the number of access points that are simultaneously in communication with the monitoring device is insufficient or the resulting location data is not sufficiently accurate. When not in use, the GPS receiver may be in a deep sleep mode or completely powered down. One or more sensing devices (416) may be used to obtain measurements from the monitored asset (102) or the surrounding environment. These sensing devices may include, but are not limited to, pressures sensors for gas and/or liquid applications, air or gas leak sensors, fill level sensors e.g., for storage tanks, valve position sensors (e.g., to monitor the function of valves), weight and/or strain sensors (including bending, torsion, etc.), and temperature sensors, spectroscopy sensors (to perform chemical analyses beyond basic gas sensing), energy usage or delivery sensors, etc. The one or more sensing devices (416) may be interfaced with the processor (412) using digital and/or analog interfaces.

In one or more embodiments of the invention, the monitoring device (400) is further equipped with a control interface (not shown). The control interface may include analog or digital outputs, including communication bus systems, and/or relays, motors, or any other equipment that may be used to control functions of the monitored asset (102) and/or other components in vicinity of the monitored asset. Those skilled in the art will appreciate that the control interface may be used to control any function of the monitored asset or functions of other components in the monitored environment.

The optionally present peripheral sensor transceiver (418), in one embodiment of the invention, establishes a data link to one or more peripheral sensors, such as the sensor discussed below, with reference to FIG. 5. The data link may be very low power, limited to a range of only, for example, three to six feet. A transmission frequency may be in a range suitable to penetrate tissue. Highly power efficient circuits (such as class C amplification) may be used to minimize power consumption, in particular on the side of the peripheral sensor, which may need to operate using small batteries. The data link may use a communication protocol analogous to the protocol further described below with reference to FIG. 6, although a simplified version (e.g., fewer communication slots) may be provided.

In one or more embodiments of the invention, the components of the monitoring device are battery powered. The battery (424) may be a rechargeable or a non-rechargeable battery that may or may not be replaceable, selected to power the components of the monitoring device for a specified duration, e.g., for multiple months or years. If the battery is rechargeable, a power or charge controller (426) may control the charging of the battery, e.g., from solar cells (422) or other external power sources, such as inductively provided power. The power/charge controller may further communicate battery status information to the processor (412). This status information may be communicated to an access point, e.g., when a low battery level is detected. In addition, the battery level may directly govern the operation of the monitoring device. For example, when a low battery level is detected, the communication frequency may be reduced, certain sensors may be deactivated, etc. External power supplies may be used, e.g., if the monitoring device is stationary.

Figure 5:
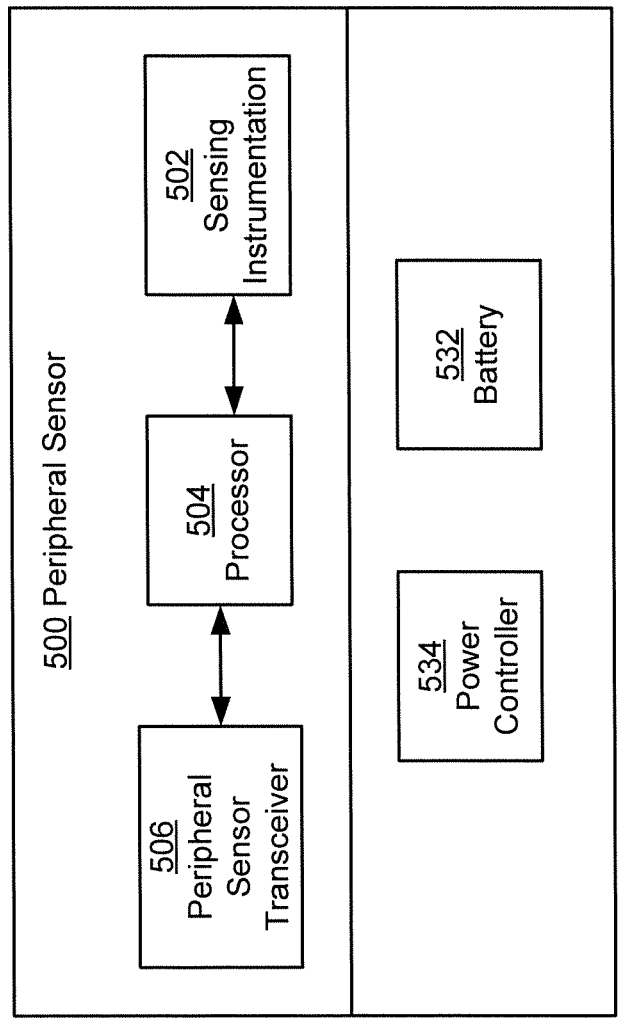
FIG. 5 shows a peripheral sensor of a system for monitoring assets, in accordance with one or more embodiments of the invention.

FIG. 5 shows a peripheral sensor, in accordance with one or more embodiments of the invention. The peripheral sensor (500) may include a sensing instrumentation (502), electronic circuits (510), an antenna (522) and a battery (532). Depending on the environment for which the peripheral sensor (400) is designed, the peripheral sensor may be hermetically sealed e.g., to prevent fluids from entering the sensor. The sensing instrumentation may include, but is not limited to, pressures sensors for gas and/or liquid applications, air or gas leak sensors, fill level sensors e.g., for storage tanks, valve position sensors (e.g., to monitor the function of valves), weight and/or strain sensors (including bending, torsion, etc.), and temperature sensors, spectroscopy sensors (to perform chemical analyses beyond basic gas sensing), energy usage or delivery sensors, etc. Consider, for example, the application of monitoring devices and peripheral sensors in mining, refining or industrial environments. The peripheral sensors may include gas sensors, configured to provide early hazard warnings to workers, on an individual basis. Alternatively, in another scenario, a monitoring device is used to monitor the fill level of a storage tank. A peripheral sensor, interfacing with the monitoring device, may further monitor a pump to monitor vibration, energy consumption, including static and transient energy consumption, and/or to control the pump, and thus, indirectly, the fill level of the storage tank. Those skilled in the art will appreciate that the peripheral sensor, when equipped with a control interface, may be used to control any function of the monitored asset or functions of other components in the monitored environment.

The electronic circuits (510), in accordance with one or more embodiments of the invention, include a processor (504) and a peripheral sensor transceiver (506). The processor (504) may be a particularly energy-efficient unit such as a microcontroller that may be implemented as a system on a chip (SOC). The processor may be selected based on computational requirements and battery life requirements. Temporarily used peripheral sensors may only need to remain operative for a few days, whereas permanently installed versions of the peripheral sensor may need to be operational for the lifetime of the monitored asset. The peripheral sensor transceiver (506) is configured to interface the peripheral sensor with the monitoring device (400) over a short distance using a low-power signal with minimal power requirements, in order to communicate the collected peripheral data to the monitoring device, from where it may be forwarded to an access point.

The battery (532) may be a rechargeable or a non-rechargeable battery, selected to power the components of the peripheral sensor for a specified duration, ranging from a few days to the lifetime of the asset. If the battery is rechargeable, a power controller (534) may control the charging of the battery from inductively provided power. The power controller may further communicate battery status information to the processor (504). This status information may be communicated to an access point, e.g., when a low battery level is detected. In addition, the battery level may directly govern the operation of the peripheral sensor. For example, when a low battery level is detected, the communication frequency may be reduced, certain sensors may be deactivated, etc.

Turning to FIG. 6, an IoT communication protocol overlay, in accordance with one or more embodiments of the invention, is shown. The IoT communication protocol overlay is designed to enable the distribution of an accurate time base by an access point to monitoring devices or other devices communicating with the access point. The IoT communication protocol overlay further establishes rules for data exchanges in the form of frequency bands and time slots to be used for communications, to reduce or eliminate collisions that may otherwise occur when multiple monitoring devices attempt to simultaneously transmit data. In one or more embodiments of the invention, the IoT communication protocol overlay may be used to extend existing IoT protocols such as LoRa or SigFox, but also other protocols such as the 802.11 Wi-Fi protocol. FIG. 6 shows an IoT communication protocol overlay (600) in which a superframe (602) and frames (604) are established. The beginning of each frame is marked by a beacon (612), emitted by the access point. A beacon may include or may be followed by a communication of various data to the IoT devices within the range of the access point. The data may include a precise time base that the access point may have obtained from its GPS unit. The data may further include a specification of the IoT communication protocol overlay, thus informing the IoT devices that are supposed to communicate with the access point of the timing and frequency of time slots assigned to them for data transmission.

The beacon may then be followed by transmissions of sensor data in the communication slots (616). Each communication slot may be of a fixed duration and may be located at a set frequency. In the exemplary IoT communication protocol overlay (600) of FIG. 6, a frame includes 24 communication slots. Groups of 8 communication slots may be simultaneously transmitted using different frequencies. Communication slots may be assigned in any way. For example, a communication by a particular IoT device may be performed using a single assigned communication slot or, if necessary, multiple communication slots that may occur in parallel at different frequencies (channels) and/or subsequently. No communication slot may be assigned to multiple devices to prevent communication collisions. A frame (x04) ends with a beacon guard time (x14), during which no communications by any of the IoT devices that rely on the IoT communication protocol overlay may be allowed. However, other IoT devices that are merely capable of communicating using the underlying IoT communication protocol, but not the IoT communication protocol overlay, may communicate during the beacon guard time.

In total, the IoT communication protocol overlay (600) provides 72 communication slots (616). Accordingly, up to 72 individual communications may be performed in a single superframe (602). If these 72 communications are insufficient to serve all IoT devices, the protocol overlay may be modified in various ways without departing from the invention. For example, a superframe may be configured to include more than three frames. Additionally or alternatively, a frame may include more than three consecutive communication slots, and/or additional frequencies (channels) may be used to allow simultaneous transmission of additional communication slots. The same IoT communication protocol overlay may be used by all access points across a site.

In one or more embodiments of the invention, not all channels that are available in the underlying IoT communication protocol are used by the IoT communication protocol overlay. Channels that are not made available may be used to support devices that are not designed to work with the IoT communication protocol overlay, while being able to use the underlying IoT protocols. Such channels may also be used for lengthy transmissions such as a firmware provided over the air.

FIG. 7 shows a computing system in accordance with one or more embodiments of the invention. Embodiments of the invention may be implemented on a computing system. Any combination of mobile, desktop, server, embedded, or other types of hardware may be used. For example, as shown in FIG. 7, the computing system (700) may include one or more computer processor(s) (702), associated memory (704) (e.g., random access memory (RAM), cache memory, flash memory, etc.), one or more storage device(s) (706) (e.g., a hard disk, an optical drive such as a compact disk (CD) drive or digital versatile disk (DVD) drive, a flash memory stick, etc.), and numerous other elements and functionalities. The computer processor(s) (702) may be an integrated circuit for processing instructions. For example, the computer processor(s) may be one or more cores, or micro-cores of a processor. The computing system (700) may also include one or more input device(s) (710), such as a touchscreen, keyboard, mouse, microphone, touchpad, electronic pen, or any other type of input device. Further, the computing system (700) may include one or more output device(s) (708), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (700) may be connected to a network (712) (e.g., a local area network (LAN), a wide area network (WAN) such as the Internet, mobile network, or any other type of network) via a network interface connection (not shown). The input and output device(s) may be locally or remotely (e.g., via the network (712)) connected to the computer processor(s) (702), memory (704), and storage device(s) (706). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform embodiments of the invention.

Further, one or more elements of the aforementioned computing system (700) may be located at a remote location and connected to the other elements over a network (712). Further, embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

Figure 8:
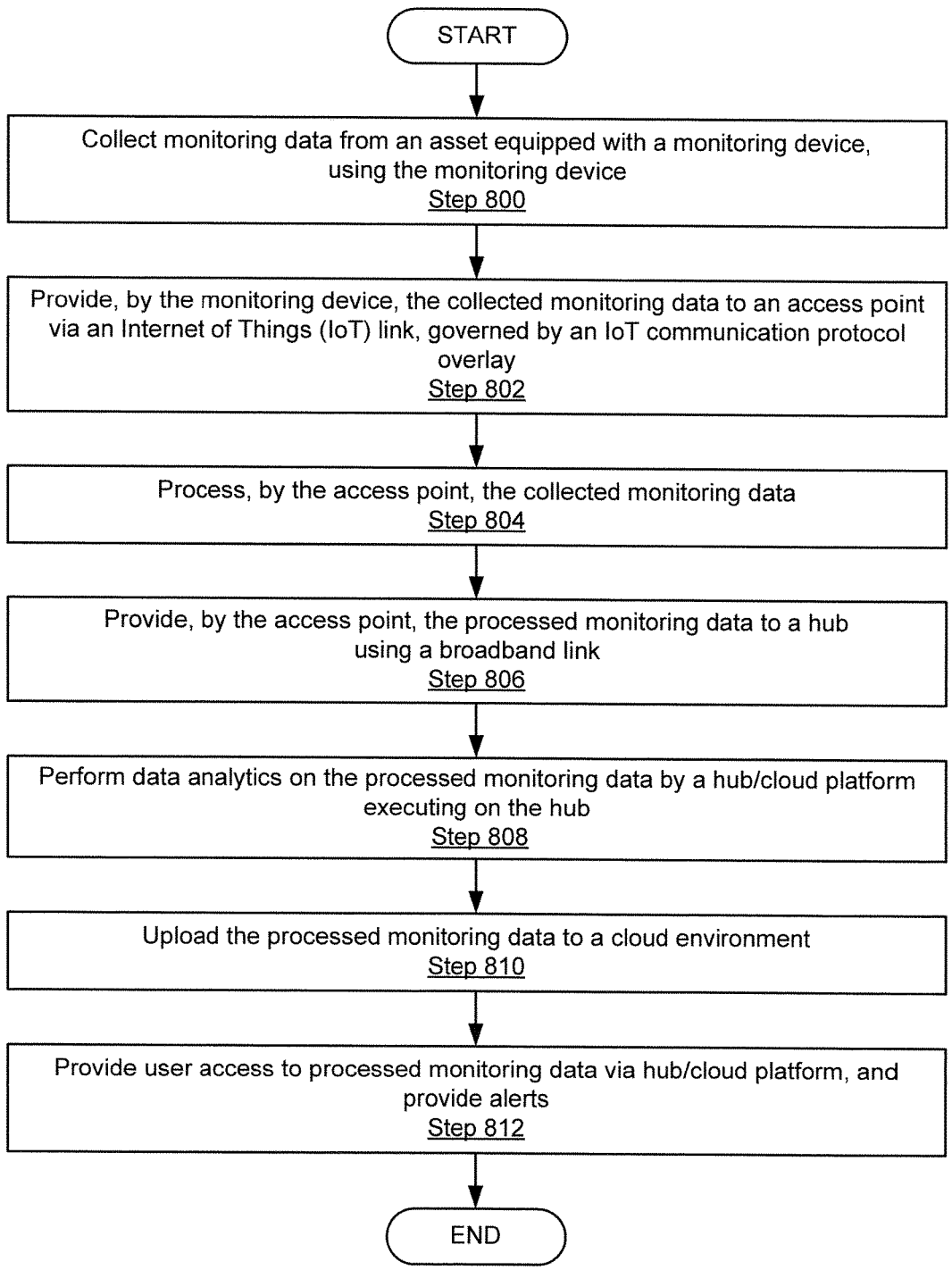
FIG. 8 shows a flowchart describing methods for monitoring assets, in accordance with one or more embodiments of the invention.

FIG. 8 shows a flowchart describing methods for monitoring assets, in accordance with one or more embodiments of the invention. The method may be used, for example, to track the location of persons or equipment and/or physiological signals of tracked individuals. The method may be executed repeatedly over time, thus enabling a user to continuously monitor the assets and to detect changes, e.g., when the assets move, when their state changes or environmental conditions change, etc.

In Step 800, monitoring data is collected from the assets that are equipped with monitoring devices. Data may be collected from the various sensors of a monitoring device, but also from peripheral sensors, if peripheral sensors are used. The collection may occur as scheduled, e.g., based on the time-base provided by the IoT communication protocol overlay or spontaneously, e.g., upon request or when a particular event is detected. The data collection by one monitoring device may be independent from the data collection by other monitoring devices. The collected data may be buffered by the monitoring device until it can be transmitted to an access point.

In Step 802, the monitoring devices provide the collected data to one or more access points, using the IoT link. Each monitoring device uses a communication slot at a particular time and in a particular frequency band, as specified by the IoT communication protocol overlay, thus avoiding transmission interference by multiple monitoring devices using the same communication slot. The transmissions of the monitoring devices may be received by one or more access points within range.

In Step 804, the received data may be processed by the access point(s) that received the data. The processing may include aggregating, filtering, fusing, compressing and/or encrypting the data. The processing may further include the exchange of data with other access points. For example, TDOA data may be exchanged between access points to determine a location of a tag sensor, relative to the access points.

In Step 806, the processed data are provided to a hub, using the broadband link that interfaces the access point(s) and the hub. Step 806 is optional and is executed only if a hub exists in the used system configuration. If no hub exists, the processed data may alternatively be provided to the cloud. Regardless of whether the system is configured to use a hub, a cloud or both, the processed data is received by the hub/cloud platform which is executing on the hub, in the cloud, or on the hub and in the cloud.

In Step 808, data analytics are performed by the hub/cloud platform executing on the hub. The data analytics may include modules that are generic to a variety of applications such as location tracking, and other modules that are specific to a particular application, such as equipment tracking in the oil & gas industry, monitoring physiological parameters of patients, etc. The data analytics may additionally or alternatively be performed in the cloud.

In Step 810, the processed monitoring data is uploaded to the cloud. This step may be performed in systems that include a cloud environment and in systems that include a combination of the hub and the cloud. Accordingly, data obtained from the tag sensors may be equally accessible via the cloud and via the hub.

In Step 812, a user is provided access to the processed monitoring data using the hub/cloud platform that is executing on the hub, in the cloud, or on the hub and in the cloud. The user may access the processed monitoring data using any type of computing device that is capable of interfacing with the hub/cloud platform. The user may obtain a visualization of the processed monitoring data, which may include text, graphics, charts, etc. The user may access a time history of the processed monitoring data and may further also access the unprocessed or partially processed data obtained from the tag sensors. Alerts may be provided to the user under certain configurable conditions. For example, an alert may be provided if a tracked equipment is leaving a particular area such as a parking lot, if unusual movement patterns (such as the lack of movement of an elderly patient, indicating a potential problem) are detected, or if physiological measurements are beyond a specified range.

Various embodiments of the invention have one or more of the following advantages. Embodiments of the invention enable comprehensive monitoring of physical assets. The monitoring may include monitoring of asset location and numerous other measurements obtained from the asset or the environment surrounding the asset. The coverage provided by the monitoring system, in accordance with one or more embodiments of the invention, is scalable, from small spaces to tens of thousands of acres. The number of assets being monitored by the monitoring system, in accordance with one or more embodiments of the invention, is scalable, e.g., from a few assets to hundreds of thousands of assets in indoor, outdoor or mixed environments. Further, depending on the nature of the assets to be monitored, different monitoring devices may be relied upon. These monitoring devices are suitable for the monitoring of stationary and moving assets, equipment, goods, animals, humans, etc. Various components of the monitoring system may be operated on battery and/or solar power, with no access to the power grid and under hostile conditions including, but not limited to broad temperature ranges, wind, rain, dust, insects and mechanical stress, in accordance with one or more embodiments of the invention. Monitoring systems, in accordance with one or more embodiments of the invention, may be operated in environments that offer hardwired, wireless or no broadband Internet access.

The following use case scenarios are intended to provide examples of possible applications of the system for monitoring physical assets, in accordance with one or more embodiments of the invention. The use case scenarios are for illustrative purposes only, and the system for monitoring physical assets is not limited to the applications discussed below.

Use Case I: Oil & Gas Industry

In one embodiment of the invention, the monitoring system is used in the oil and/or gas industry. Non-stationary equipment, such as vehicles, may be tracked using monitoring devices, thus allowing monitoring location and appropriate use at any time. Further, stationary equipment, such as pumps, pipelines, storage tanks, etc., may also be monitored and/or controlled using monitoring devices. For example, monitoring devices equipped with appropriate sensors may measure flow, pressure, the presence of gasses, fill level, temperature, etc. In addition, monitoring devices may be used to remotely control equipment. For example, pumps may be remotely activated and deactivated, their power level may be adjusted, valves may be opened or closed, lights may be turned on and off, etc. The monitoring system, thus, facilitates smooth operation and productivity in the oil and/or gas industry.

Use Case II: Healthcare

In one embodiment of the invention, the monitoring system is used in healthcare. Patients' locations may be tracked using monitoring devices, which may be advantageous when monitoring elderly patients, patients with behavioral problems and/or patients suffering from memory loss, loss of orientation, etc. Further, the monitoring devices and/or peripheral sensors interfacing with the monitoring devices may also be used to obtain physiological parameters from patients. These physiological parameters may include, but are not limited to, heart rate, blood pressure, blood sugar, body temperature, movement patterns, etc. The monitoring system thus helps ensuring the wellbeing of patients Use Case III: Vehicle Dealerships, Rental Car Agencies In one embodiment of the invention, the monitoring system is used to track vehicles of vehicle dealers and/or rental car agencies. Numerous vehicles may be kept in large lots, and these vehicles may be located and tracked at any time, using the monitoring system. Such tracking may discourage unauthorized vehicle use by employees, thereby reducing losses due to use, wear and accidents. In addition, vehicles may also be tracked when taken on test drives by potential buyers, to ensure that these vehicles are not excessively used during the test drives. The monitoring system may thus facilitate operation of vehicle dealerships or rental car agencies and/or reduce cost.

Use Case IV: Campus Management & Security

In one embodiment of the invention, the monitoring system is used to track individuals on a campus, such as a university campus, a public location, a museum, a library, a factory, a park, etc. Individuals may be visitors, employees, security staff, etc. The tag sensor or in vivo-type sensor may be placed on the students, for example, and information may be transmitted about the student's exact location at all times, even inside buildings where GPS is unavailable. Knowing the location of an individual may be beneficial for security purposes, e.g., doors may be locked and unlocked based on the location of tracked individuals. Further, information may be provided to the tracked individuals in a location-dependent manner, thereby improving campus visitor experience, increase security and streamline operations.

Use Case V: Agriculture

In one or more embodiments of the invention, the monitoring system described herein may be used in the agriculture industry. For example, sensor such as those described above may be used to obtain information about the fertility of soil and moisture content of soil. The system may be used specifically to conserve energy water resources and detection of water levels to enhance crop productivity. Selection methods for controlling irrigation based on different parameters may then be learned and applied. Specifically, tags may be placed on water tanks to track the amount of water inside. Tags may also be placed on non-stationary farming equipment to know the exact location of such equipment in a large agricultural field. In addition, drones may be used across the agricultural fields, where the drones are configured to house/carry the access points that communicate with the sensors on the crops and/or in the soil.

Use Case VI: Warehousing

In one embodiment of the invention, the monitoring system is used to track equipment, goods, shipments etc. The tracked equipment may include, but is not limited to forklifts, other types of vehicles, tools, etc. Further, a similar configuration may be used in other settings as well, for example in a baggage processing facility of an airport in order to track luggage as it is progressing through the facility. Such a system may result in a reduction in lost luggage. The monitoring system may further be used to detect bottlenecks, to strategically move equipment to locations where it is needed, etc., thus improving overall operations.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system for monitoring physical assets in a monitored environment, the system comprising:
    monitoring devices attached to monitored physical assets, and configured to collect monitoring data from the monitored physical assets;
    a first access point, configured to receive the collected monitoring data from the monitoring devices and to process the collected monitoring data;
    an Internet of Things (IoT) link established between each of the monitoring devices and the first access point;
    an IoT communication protocol overlay that enables synchronized uplinks from the monitoring devices to the first access point via the IoT links,
        wherein the IoT communication protocol overlay governs transmissions of collected monitoring data by the monitoring devices to the first access point; and
    a hub/cloud platform configured to:
        receive the processed monitoring data from the first access point;
        perform data analytics on the processed monitoring data; and
        provide a user interface that enables a user to monitor the physical assets.

2. The system of claim 1, further comprising:
a second access point; and
a third access point,
    wherein IoT link coverages of the first, the second and the third access points overlap in an overlap region of the monitored environment,
    wherein one of the monitoring devices of a monitored physical asset in the overlap region performs a transmission, using the IoT communication protocol overlay,
    wherein the transmission is received by the first, the second, and the third access points,
    wherein the first, the second, and the third access points estimate a distance of the monitoring device from the first, the second and the third access points, respectively, using time difference of arrival (TDOA) methods, and
    wherein the system estimates a location of the monitoring device, based on the three distances, using triangulation, and wherein the estimated location is included in the processed monitoring data received by the hub/cloud platform.

3. The system of claim 1, where the system estimates a location of one of the monitoring devices using received signal strength indication (RSSI) methods.

4. The system of claim 1, where a location of one of the monitoring devices is obtained using a GPS unit of the monitoring device.

5. The system of claim 1, further comprising a cloud environment configured to provide analytics services to the user via the hub/cloud platform, wherein the cloud environment is operatively connected to the first access point.

6. The system of claim 1, further comprising a hub, configured to establish an interface between the first access point and a cloud environment,
wherein the hub/cloud platform jointly executes on the hub and in the cloud environment to provide analytics services to the user.

7. The system of claim 6,
wherein the analytics services comprise physiological analytics that enable the user to monitor a well-being of at least one of the physical assets, and
wherein the at least one physical assets is a person.

8. The system of claim 7, wherein the analytics services are configured to trigger an alert when the well-being of the person is found to be at risk.

9. The system of claim 6, wherein the execution of the hub/cloud platform is at least partially redundant, enabling the user to access hub/cloud functionality via the hub or via the cloud.

10. The system of claim 1, wherein one of the monitoring devices comprises:
sensors configured to obtain measurements from the monitored physical assets equipped with the monitoring devices;
a processor configured to process the obtained measurements;
an IoT transceiver, configured to transmit the processed measurements to the first access point;
a battery that powers the monitoring device; and
a fastener configured to affix the monitoring device to the monitored asset.

11. The system of claim 10, wherein the monitoring device further comprises an RFID tag, programmed with an identifier of the monitored asset that can be read out by an RFID reader in proximity of the monitored asset.

12. The system of claim 10, wherein the sensors comprise at least one selected from a group consisting of a pressure sensor, a gas sensor, a tank fill level sensor, a valve position sensor, a weight sensor, a strain sensor and a temperature sensor.

13. The system of claim 10, wherein the monitoring device further comprises a control interface configured to control one selected from a group consisting of a function of the monitored asset and a component in the monitored environment.

14. The system of claim 10, further comprising a peripheral sensor configured to obtain at least one additional measurement from the monitored assets, wherein the at least one additional measurement is provided to the monitoring device, which relays the at least one additional measurement to the first access point, and
wherein the monitoring device comprises a peripheral sensor transceiver configured to receive the at least one additional measurement.

15. The system of claim 14, wherein the peripheral sensor comprises at least one selected from the group consisting of a pressure sensor, a gas sensor, a tank fill level sensor, a valve position sensor, a weight sensor, a strain sensor, a temperature sensor, a spectroscopy sensor, and an energy consumption sensor.

16. The system of claim 10, wherein the peripheral sensor further comprises a control interface configured to control one selected from a group consisting of a function of the monitored asset and a component in the monitored environment.

17. The system of claim 1, wherein the first access point is further configured to provide a broadband data interface to broadband equipment in the monitored environment.

18. The system of claim 17, wherein the broadband equipment comprises at least one selected from a group consisting of a drone, a camera, a laptop and a smartphone.

19. The system of claim 1, wherein the processing of the collected monitoring data comprises at least one selected from a group consisting of monitoring device data aggregation, monitoring device data filtering, monitoring device data fusion, monitoring device data compression and monitoring device data encryption.

20. The system of claim 1,
wherein the first access point is installed on a first site of the monitored environment and
wherein a second access point is installed on a second site of the monitored environment, separate from the first site,
thereby establishing a multi-site monitoring system.

21. The system of claim 1, configured to separately monitor a first subset of the monitored assets associated with a first tenant, and a second subset of the monitored assets associated with a second tenant, thereby establishing a multi-tenant monitoring system.

22. A system for monitoring physical assets in a monitored environment, the system comprising:
a two-tier access point comprising a first tier broadband communication interface and a second tier narrowband communication interface, and configured to:
receive, using the narrowband interface, monitoring data from monitoring devices that are attached to monitored assets and configured to collect the monitoring data from the monitoring devices that are attached to the monitored assets; and
transmit, using the broadband interface, the received monitoring data to a hub/cloud platform that provides a user interface enabling a user to monitor the physical assets.

23. The system of claim 22, wherein the second tier narrowband communication interface is an Internet of Things (IoT) interface.

24. The system of claim 23, wherein the IoT interface is based on one selected from a group consisting of a LoRa and a SigFox protocol.

25. The system of claim 22, wherein the first tier broadband communication interface is a wireless local area network (WLAN).

26. The system of claim 25, wherein the WLAN is based on the Wi-Fi standard.

27. The system of claim 22, further comprising additional two tier access points, wherein the two-tier access point and the additional two tier access points interface using the first tier broadband communication interface.

28. The system of claim 27, wherein the interfacing two tier access point and the additional two-tier access points form a mesh.

29. The system of claim 28, wherein the two tier access point is a primary access point, providing an uplink, and each of a subset of the additional two tier access points directly interfaces with the primary access point.

30. The system of claim 28, wherein the two tier access point is a primary access point, providing an uplink, and a subset of the additional two tier access points interface with the primary access point in a daisy-chain configuration.

31. The system of claim 27, wherein the two tier access point and the additional two tier access points provide a spatially overlapping coverage in a region, enabling a monitoring device to simultaneously communicate with at least three of the two tier access points.

32. The system of claim 27, further comprising a hub providing an uplink to a cloud environment, wherein the hub/cloud platform executes on at least one selected from a group consisting of the hub and the cloud environment.

* * * * *